(12) United States Patent
Pedro et al.

(10) Patent No.: US 11,331,446 B2
(45) Date of Patent: *May 17, 2022

(54) VENTILATION MASK

(71) Applicant: Revolutionary Medical Devices, Inc., Tucson, AZ (US)

(72) Inventors: Michael J. Pedro, Brooklyn, NY (US); Steven H. Cataldo, New York, NY (US); David M. Kane, Tucson, AZ (US); Thomas Reilly, Tucson, AZ (US); Ryan Redford, Tucson, AZ (US)

(73) Assignee: Revolutionary Medical Devices, Inc., Tucson, AZ (US)

( * ) Notice: Subject to any disclaimer, the term of this patent is extended or adjusted under 35 U.S.C. 154(b) by 199 days.

This patent is subject to a terminal disclaimer.

(21) Appl. No.: 15/127,759

(22) PCT Filed: Jun. 10, 2016

(86) PCT No.: PCT/US2016/037070
§ 371 (c)(1),
(2) Date: Sep. 20, 2016

(87) PCT Pub. No.: WO2016/201358
PCT Pub. Date: Dec. 15, 2016

(65) Prior Publication Data
US 2018/0193582 A1    Jul. 12, 2018

Related U.S. Application Data

(60) Provisional application No. 62/324,197, filed on Apr. 18, 2016, provisional application No. 62/319,686, (Continued)

(51) Int. Cl.
*A61M 16/06*     (2006.01)
*A61M 16/00*     (2006.01)
(Continued)

(52) U.S. Cl.
CPC ......... *A61M 16/0616* (2014.02); *A61B 5/082* (2013.01); *A61M 16/009* (2013.01);
(Continued)

(58) Field of Classification Search
CPC .............. A61M 16/06; A61M 16/0672; A61M 16/009; A61M 16/085; A61M 2230/432;
(Continued)

(56) References Cited

U.S. PATENT DOCUMENTS

| 1,050,621 A | 1/1913 | Ford .................... 128/206.28 |
| 1,131,802 A | 3/1915 | Stenshoel |

(Continued)

FOREIGN PATENT DOCUMENTS

| CN | 2631528 Y | 8/2004 |
| CN | 201101786 Y | 8/2008 |

(Continued)

OTHER PUBLICATIONS

Partial Supplementary European Search Report for Application No. 16808466.3, dated Jan. 22, 2019, 14 pages.

(Continued)

*Primary Examiner* — Victoria Murphy
(74) *Attorney, Agent, or Firm* — Morgan, Lewis & Bockius LLP

(57) ABSTRACT

A nasal ventilation mask having one or more attachment ports located adjacent to and overlying an upper lip of a patient when worn.

12 Claims, 24 Drawing Sheets

Related U.S. Application Data filed on Apr. 7, 2016, provisional application No. 62/308,127, filed on Mar. 14, 2016, provisional application No. 62/301,359, filed on Feb. 29, 2016, provisional application No. 62/298,295, filed on Feb. 22, 2016, provisional application No. 62/298,265, filed on Feb. 22, 2016, provisional application No. 62/286,165, filed on Jan. 22, 2016, provisional application No. 62/255,120, filed on Nov. 13, 2015, provisional application No. 62/253,528, filed on Nov. 10, 2015, provisional application No. 62/253,512, filed on Nov. 10, 2015, provisional application No. 62/253,520, filed on Nov. 10, 2015, provisional application No. 62/245,794, filed on Oct. 23, 2015, provisional application No. 62/245,810, filed on Oct. 23, 2015, provisional application No. 62/204,899, filed on Aug. 13, 2015, provisional application No. 62/174,410, filed on Jun. 11, 2015.

(51) Int. Cl.

| | | |
|---|---|---|
| *A61M 16/08* | (2006.01) | |
| *A61B 5/08* | (2006.01) | |
| *A61M 16/22* | (2006.01) | |
| *A61M 16/01* | (2006.01) | |
| *A61M 16/20* | (2006.01) | |
| *A61M 16/16* | (2006.01) | |
| *A61M 16/04* | (2006.01) | |
| *A61B 1/00* | (2006.01) | |
| *A61B 1/267* | (2006.01) | |
| *A61B 5/097* | (2006.01) | |
| *A61M 16/10* | (2006.01) | |

(52) U.S. Cl.
CPC ........ *A61M 16/06* (2013.01); *A61M 16/0605* (2014.02); *A61M 16/0666* (2013.01); *A61M 16/0672* (2014.02); *A61M 16/085* (2014.02); *A61M 16/22* (2013.01); *A61B 1/00154* (2013.01); *A61B 1/267* (2013.01); *A61B 5/097* (2013.01); *A61M 16/01* (2013.01); *A61M 16/0488* (2013.01); *A61M 16/0683* (2013.01); *A61M 16/161* (2014.02); *A61M 16/20* (2013.01); *A61M 16/208* (2013.01); *A61M 16/209* (2014.02); *A61M 2016/003* (2013.01); *A61M 2016/0027* (2013.01); *A61M 2016/0033* (2013.01); *A61M 2016/103* (2013.01); *A61M 2016/1025* (2013.01); *A61M 2016/1035* (2013.01); *A61M 2202/0208* (2013.01); *A61M 2205/3331* (2013.01); *A61M 2205/3368* (2013.01); *A61M 2205/7518* (2013.01); *A61M 2210/0618* (2013.01); *A61M 2210/0625* (2013.01); *A61M 2230/432* (2013.01); *A61M 2230/435* (2013.01); *A61M 2230/437* (2013.01)

(58) Field of Classification Search
CPC . A61M 2016/103; A61M 16/01; A61B 5/082; A61B 5/097
See application file for complete search history.

(56) References Cited

U.S. PATENT DOCUMENTS

| | | | |
|---|---|---|---|
| 1,441,817 A | 1/1923 | McCullough | |
| 1,729,525 A | 9/1929 | Stenshoel | |
| 1,776,167 A | 9/1930 | Stenshoel | |
| 2,452,816 A | 11/1948 | Wagner | 311/10 |
| 2,843,121 A | 7/1958 | Hudson | 128/146 |
| 2,939,458 A * | 6/1960 | Lundquist | A62B 18/025 128/206.25 |
| 3,013,556 A | 12/1961 | Galleher | |
| 3,522,612 A | 8/1970 | Palmer | 2/88 |
| 3,556,097 A | 1/1971 | Wallace | 128/188 |
| 3,670,726 A * | 6/1972 | Mahon | A61M 16/08 128/204.18 |
| 3,779,164 A | 12/1973 | Study | 128/206 |
| 3,815,596 A | 6/1974 | Keener et al. | 128/188 |
| 3,856,051 A | 12/1974 | Bain | 138/114 |
| 3,889,668 A | 6/1975 | Ochs et al. | 128/134 |
| 3,897,777 A | 8/1975 | Morrison | 128/133 |
| D242,490 S | 11/1976 | Belkin | D83/1 R |
| 4,005,499 A | 2/1977 | Klein | 5/485 |
| 4,007,737 A | 2/1977 | Paluch | 128/188 |
| 4,015,598 A | 4/1977 | Brown | 128/188 |
| 4,188,946 A | 2/1980 | Watson et al. | 128/204.22 |
| D256,161 S | 7/1980 | Oliver | D6/602 |
| 4,231,363 A * | 11/1980 | Grimes | A61M 16/06 128/205.25 |
| 4,232,667 A | 11/1980 | Chalon et al. | 128/203.26 |
| 4,248,218 A | 2/1981 | Fischer | 128/204.18 |
| 4,259,757 A | 4/1981 | Watson | 5/434 |
| 4,265,235 A | 5/1981 | Fukunaga | 128/200.24 |
| 4,265,239 A | 5/1981 | Fischer, Jr. et al. | 128/205.17 |
| 4,275,720 A | 6/1981 | Wichman | 128/853 |
| 4,328,797 A | 5/1982 | Rollins | 128/202.15 |
| 4,457,026 A | 7/1984 | Morris | 2/171 |
| 4,463,755 A | 8/1984 | Suzuki | 128/204.18 |
| 4,471,769 A | 9/1984 | Lockhart | 128/849 |
| 4,574,796 A | 3/1986 | Lundstrom | 128/855 |
| 4,596,246 A | 6/1986 | Lyall | 128/202.27 |
| 4,657,010 A | 4/1987 | Wright | 128/205.25 |
| 4,700,691 A | 10/1987 | Tari et al. | 128/1 R |
| 4,770,169 A | 9/1988 | Schmoegner et al. | 128/207.13 |
| 4,905,712 A | 3/1990 | Bowlin et al. | 128/870 |
| 5,046,200 A | 9/1991 | Feder | 2/452 |
| 5,046,491 A * | 9/1991 | Derrick | A61B 5/097 128/200.24 |
| 5,121,746 A | 6/1992 | Sikora | 128/203.12 |
| 5,167,636 A | 12/1992 | Clement | |
| D333,404 S | 2/1993 | Thompson | D6/602 |
| 5,243,971 A | 9/1993 | Sullivan et al. | 128/205.25 |
| 5,255,303 A | 10/1993 | DiMaio et al. | 378/177 |
| 5,271,390 A | 12/1993 | Gray et al. | 128/207.12 |
| 5,284,160 A | 2/1994 | Dryden | 128/203.12 |
| D347,494 S | 5/1994 | Mustelier | D24/110.4 |
| D354,128 S | 1/1995 | Rinehart | D24/110.1 |
| 5,404,873 A | 4/1995 | Leagre et al. | 128/204.18 |
| 5,462,050 A | 10/1995 | Dahlstrand | 128/207.18 |
| 5,474,060 A | 12/1995 | Evans | 128/204.22 |
| 5,485,837 A | 1/1996 | Solesbee et al. | 128/207.17 |
| 5,524,639 A | 6/1996 | Lanier et al. | 128/845 |
| D373,921 S | 9/1996 | Palomo et al. | D6/602 |
| 5,557,049 A | 9/1996 | Ratner | 128/204.23 |
| RE35,339 E | 10/1996 | Rapoport | 128/204.18 |
| 5,560,354 A | 10/1996 | Berthon-Jones et al. | 128/205.25 |
| 5,586,551 A | 12/1996 | Hilliard | 128/200.14 |
| 5,647,357 A | 7/1997 | Barnett et al. | 128/206.24 |
| 5,649,331 A | 7/1997 | Wilkinson et al. | 5/710 |
| 5,660,174 A | 8/1997 | Jacobelli | 128/206.24 |
| 5,661,859 A | 9/1997 | Schaefer | 5/621 |
| 5,685,298 A | 11/1997 | Idris | 128/206.12 |
| 5,738,094 A | 4/1998 | Hoftman | 128/206.26 |
| 5,743,253 A * | 4/1998 | Castor | A61M 16/024 128/200.24 |
| 5,746,201 A | 5/1998 | Kidd | 128/206.24 |
| 5,749,358 A | 5/1998 | Good et al. | 128/205.23 |
| 5,778,872 A | 7/1998 | Fukunaga et al. | 128/202.27 |
| D402,755 S | 12/1998 | Kwok | D24/110 |
| 5,857,460 A | 1/1999 | Popitz | |
| 5,884,624 A | 3/1999 | Barnett et al. | 128/206.24 |
| 5,933,886 A | 8/1999 | Washington | 5/494 |
| 5,966,763 A | 10/1999 | Thomas et al. | 5/715 |
| 5,975,079 A | 11/1999 | Hellings et al. | 128/206.24 |
| 5,983,896 A | 11/1999 | Fukunaga et al. | 128/207.14 |
| 6,003,511 A | 12/1999 | Fukunaga et al. | 128/202.27 |
| 6,019,101 A | 2/2000 | Cotner et al. | 128/207.13 |

(56) References Cited

U.S. PATENT DOCUMENTS

| | | | | |
|---|---|---|---|---|
| 6,035,852 | A | 3/2000 | Hoftman | 128/206.26 |
| 6,058,933 | A | 5/2000 | Good et al. | 128/205.13 |
| D428,987 | S | 8/2000 | Kwok | D24/110.1 |
| 6,112,746 | A | 9/2000 | Kwok et al. | 128/207.13 |
| 6,123,071 | A | 9/2000 | Berthon-Jones et al. | 128/204.18 |
| 6,129,082 | A | 10/2000 | Leagre | 128/205.29 |
| 6,152,137 | A | 11/2000 | Schwartz et al. | 128/846 |
| D435,650 | S | 12/2000 | Kwok | D24/110.1 |
| 6,192,876 | B1 | 2/2001 | Denyer et al. | |
| 6,192,886 | B1 * | 2/2001 | Rudolph | A61M 16/06 128/205.25 |
| 6,216,691 | B1 | 4/2001 | Kenyon et al. | 128/205.18 |
| 6,263,874 | B1 * | 7/2001 | LeDez | A61M 16/009 128/205.25 |
| 6,342,040 | B1 | 1/2002 | Starr et al. | 600/538 |
| 6,357,441 | B1 | 3/2002 | Kwok et al. | 128/207.13 |
| 6,397,847 | B1 | 6/2002 | Scarberry et al. | 128/206.24 |
| 6,401,713 | B1 | 6/2002 | Hill et al. | 128/204.21 |
| 6,412,487 | B1 | 7/2002 | Gunaratnam et al. | 128/206.24 |
| 6,412,488 | B1 | 7/2002 | Barnett et al. | 128/207.13 |
| 6,439,230 | B1 | 8/2002 | Gunaratnam et al. | 128/206.21 |
| 6,439,231 | B1 | 8/2002 | Fukunaga et al. | 128/207.14 |
| 6,446,288 | B1 | 9/2002 | Pi | 5/636 |
| 6,459,923 | B1 | 10/2002 | Plewes et al. | 600/411 |
| 6,463,931 | B1 | 10/2002 | Kwok et al. | 128/207.11 |
| 6,467,483 | B1 | 10/2002 | Kopacko et al. | 128/207.12 |
| D467,345 | S | 12/2002 | Gingles et al. | D24/189 |
| 6,513,526 | B2 | 2/2003 | Kwok et al. | 128/206.24 |
| 6,520,182 | B1 | 2/2003 | Gunaratnam | 128/206.27 |
| 6,581,602 | B2 | 6/2003 | Kwok et al. | 128/307.13 |
| 6,584,977 | B1 | 7/2003 | Serowski | 128/206.24 |
| 6,612,306 | B1 | 9/2003 | Mault | 128/204.22 |
| 6,615,835 | B1 | 9/2003 | Cise | 128/200.26 |
| 6,626,178 | B2 | 9/2003 | Morgan et al. | 128/206.26 |
| 6,631,713 | B1 | 10/2003 | Christopher | 128/200.21 |
| 6,631,718 | B1 | 10/2003 | Lovell | 128/206.24 |
| 6,634,358 | B2 | 10/2003 | Kwok et al. | 128/205.25 |
| 6,651,663 | B2 | 11/2003 | Barnett et al. | 128/207.13 |
| 6,694,973 | B1 | 2/2004 | Dunhao et al. | 128/203.12 |
| 6,701,927 | B2 | 3/2004 | Kwok et al. | 128/207.13 |
| 6,729,333 | B2 | 5/2004 | Barnett et al. | 128/207.13 |
| 6,736,139 | B1 | 5/2004 | Wix | 128/206.21 |
| D493,523 | S | 7/2004 | Barnett et al. | D24/110.4 |
| 6,779,524 | B2 | 8/2004 | Strawder et al. | 128/206.21 |
| 6,792,943 | B2 | 9/2004 | Kumar et al. | 128/200.26 |
| 6,796,308 | B2 | 9/2004 | Gunaratnam et al. | 128/206.24 |
| 6,805,117 | B1 | 10/2004 | Ho et al. | 128/201.22 |
| 6,832,610 | B2 | 12/2004 | Gradon et al. | 128/206.27 |
| 6,863,071 | B2 | 3/2005 | Annett et al. | 128/849 |
| 6,871,649 | B2 | 3/2005 | Kwok et al. | 128/206.24 |
| 6,892,729 | B2 | 5/2005 | Smith et al. | 128/204.18 |
| 6,895,965 | B2 | 5/2005 | Scarberry et al. | 128/206.24 |
| 6,931,664 | B1 | 8/2005 | Chen | 2/9 |
| 6,935,337 | B2 | 8/2005 | Virr et al. | 128/203.16 |
| 6,981,503 | B1 | 1/2006 | Shapiro | 128/845 |
| 7,004,168 | B2 | 2/2006 | Mace et al. | 128/206.21 |
| 7,007,696 | B2 | 3/2006 | Palkon et al. | 128/207.13 |
| 7,013,896 | B2 | 3/2006 | Schmidt | 128/206.15 |
| 7,017,576 | B2 | 3/2006 | Olsen et al. | 128/205.25 |
| 7,021,311 | B2 | 4/2006 | Gunaratnam et al. | 128/206.24 |
| 7,028,981 | B2 | 4/2006 | Horton | |
| 7,036,508 | B2 | 5/2006 | Kwok | 128/207.11 |
| 7,047,971 | B2 | 5/2006 | Ho et al. | 128/207.11 |
| 7,066,179 | B2 | 6/2006 | Eaton et al. | 128/206.27 |
| 7,069,932 | B2 | 7/2006 | Eaton et al. | 128/206.24 |
| 7,069,933 | B2 | 7/2006 | Kwok et al. | 128/206.24 |
| 7,114,498 | B1 | 10/2006 | Nashed | 128/205.27 |
| 7,152,604 | B2 | 12/2006 | Hickle et al. | |
| 7,159,587 | B2 | 1/2007 | Drew et al. | 128/204.18 |
| 7,178,524 | B2 | 2/2007 | Noble | 128/206.11 |
| 7,178,527 | B2 | 2/2007 | Kwok et al. | 128/207.13 |
| 7,210,481 | B1 | 5/2007 | Lovell et al. | 128/205.25 |
| 7,219,669 | B1 | 5/2007 | Lovell et al. | 128/206.24 |
| 7,237,551 | B2 | 7/2007 | Ho et al. | 128/207.13 |
| 7,243,651 | B2 | 7/2007 | Kwok et al. | 128/205.25 |
| 7,287,528 | B2 | 10/2007 | Ho et al. | 128/206.21 |
| 7,341,060 | B2 | 3/2008 | Ging et al. | 128/206.11 |
| 7,383,839 | B2 | 6/2008 | Porat et al. | 128/207.18 |
| 7,445,602 | B2 | 11/2008 | Yamamori | 128/201.27 |
| 7,448,386 | B2 | 11/2008 | Ho et al. | 128/206.21 |
| 7,467,431 | B2 | 12/2008 | Weedling et al. | 5/633 |
| 7,487,772 | B2 | 2/2009 | Ging et al. | 128/202.27 |
| 7,487,777 | B2 | 2/2009 | Gunaratnam et al. | 128/206.24 |
| 7,500,280 | B2 | 3/2009 | Dixon et al. | 5/713 |
| 7,500,482 | B2 | 3/2009 | Biederman | 128/206.21 |
| 7,614,398 | B2 | 11/2009 | Virr et al. | 128/203.26 |
| 7,631,644 | B2 | 12/2009 | Ho et al. | 128/206.21 |
| 7,665,464 | B2 | 2/2010 | Kopacko et al. | 128/306.24 |
| 7,669,599 | B2 | 3/2010 | Gunaratnam et al. | 128/205.25 |
| 7,700,129 | B2 | 4/2010 | Ito et al. | 424/486 |
| 7,743,767 | B2 | 6/2010 | Ging et al. | 128/206.24 |
| 7,753,051 | B2 | 7/2010 | Burrow et al. | 128/207.11 |
| 7,779,832 | B1 | 8/2010 | Ho | 128/201.22 |
| 7,841,988 | B2 | 11/2010 | Yamamori | 600/532 |
| 7,870,859 | B2 | 1/2011 | Barnett et al. | 128/204.24 |
| 7,874,292 | B2 | 1/2011 | Smith et al. | 128/206.27 |
| 7,913,337 | B1 | 3/2011 | Masson | 5/618 |
| 7,926,487 | B2 | 4/2011 | Drew et al. | 128/205.25 |
| 7,927,285 | B2 | 4/2011 | Yamamori | 600/532 |
| 7,931,024 | B2 | 4/2011 | Ho et al. | 128/206.21 |
| 7,938,117 | B2 | 5/2011 | Chiesa et al. | 128/205.25 |
| 7,950,392 | B2 | 5/2011 | Kwok et al. | 128/206.24 |
| 7,975,694 | B2 | 7/2011 | Ho | 128/207.13 |
| 7,997,267 | B2 | 8/2011 | Ging et al. | 128/202.27 |
| 8,001,968 | B2 | 8/2011 | Doty et al. | 128/205.27 |
| 8,001,970 | B2 | 8/2011 | King et al. | 128/845 |
| 8,028,699 | B2 | 10/2011 | Ho et al. | 128/206.21 |
| 8,042,539 | B2 | 10/2011 | Chandran et al. | 128/206.28 |
| 8,042,541 | B2 | 10/2011 | Amarasinghe et al. | 128/206.27 |
| 8,056,561 | B2 | 11/2011 | Kwok et al. | 128/206.24 |
| 8,132,270 | B2 | 3/2012 | Lang et al. | 2/422 |
| 8,161,971 | B2 | 4/2012 | Jaffe | 128/200.24 |
| 8,191,553 | B2 | 6/2012 | Haworth et al. | 128/845 |
| 8,210,181 | B2 | 7/2012 | Gunaratnam et al. | 128/207.11 |
| 8,261,745 | B2 | 9/2012 | Chandran et al. | 128/206.24 |
| 8,261,746 | B2 | 9/2012 | Lynch et al. | 128/206.24 |
| 8,267,091 | B2 | 9/2012 | Smith et al. | 128/202.27 |
| 8,302,224 | B2 | 11/2012 | Lehman | 5/486 |
| 8,312,883 | B2 | 11/2012 | Gunaratnam et al. | 128/207.18 |
| 8,336,142 | B1 | 12/2012 | See et al. | 5/634 |
| 8,336,549 | B2 | 12/2012 | Nashed | 128/206.28 |
| 8,347,889 | B2 | 1/2013 | Farnum | 128/845 |
| 8,365,734 | B1 | 2/2013 | Lehman | 128/206.28 |
| 8,397,724 | B2 | 3/2013 | Sher et al. | 128/205.25 |
| D681,383 | S | 5/2013 | Derman et al. | D6/603 |
| 8,443,807 | B2 | 5/2013 | McAuley et al. | 128/207.18 |
| 8,485,190 | B2 | 7/2013 | Barnett et al. | 128/206.24 |
| 8,485,192 | B2 | 7/2013 | Davidson et al. | 128/206.24 |
| 8,490,623 | B2 | 7/2013 | Berthon-Jones et al. | 128/206.21 |
| RE44,453 | E | 8/2013 | Virr et al. | 128/203.27 |
| 8,479,726 | B2 | 9/2013 | McAuley | 128/201.17 |
| 8,522,783 | B2 | 9/2013 | Kwok et al. | 128/204.26 |
| 8,528,558 | B2 | 9/2013 | Drew et al. | 128/205.25 |
| 8,550,081 | B2 | 10/2013 | Davidson et al. | 128/206.24 |
| 8,550,082 | B2 | 10/2013 | Davidson et al. | 128/206.24 |
| 8,550,083 | B2 | 10/2013 | Davidson et al. | 128/206.24 |
| 8,555,885 | B2 | 10/2013 | Davidson et al. | 128/206.24 |
| 8,567,402 | B2 | 10/2013 | Gunaratnam et al. | 128/205.25 |
| 8,567,404 | B2 | 10/2013 | Davidson et al. | 128/206.24 |
| D693,603 | S | 11/2013 | Esquivel et al. | D6/602 |
| 8,573,211 | B2 | 11/2013 | Ho et al. | 128/206.24 |
| 8,573,212 | B2 | 11/2013 | Lynch et al. | 128/206.24 |
| 8,573,213 | B2 | 11/2013 | Davidson et al. | 128/206.24 |
| 8,573,214 | B2 | 11/2013 | Davidson et al. | 128/206.24 |
| 8,573,215 | B2 | 11/2013 | Davidson et al. | 128/206.24 |
| 8,573,217 | B2 | 11/2013 | Todd et al. | 128/207.12 |
| 8,578,935 | B2 | 11/2013 | Davidson et al. | 128/206.24 |
| 8,578,939 | B1 | 11/2013 | Kimani Mwangi et al. | 128/848 |
| 8,613,280 | B2 | 12/2013 | Davidson et al. | 128/206.24 |
| 8,613,281 | B2 | 12/2013 | Davidson et al. | 128/206.24 |
| 8,616,211 | B2 | 12/2013 | Davidson et al. | 128/206.24 |
| 8,631,792 | B2 | 1/2014 | Ho et al. | 128/206.24 |

(56) References Cited

U.S. PATENT DOCUMENTS

| | | | |
|---|---|---|---|
| 8,636,006 B2 | 1/2014 | Kwok et al. | 128/207.13 |
| 8,667,965 B2 | 3/2014 | Gunaratnam et al. | 128/207.13 |
| 8,684,004 B2 | 4/2014 | Eifler | 128/206.24 |
| 8,689,366 B2 | 4/2014 | Ho | 2/452 |
| 8,707,950 B1 | 4/2014 | Rubin | 128/202.27 |
| 8,714,157 B2 | 5/2014 | McAuley et al. | 128/205.25 |
| 8,752,551 B2 | 6/2014 | Chandran et al. | 128/206.28 |
| 8,807,134 B2 | 8/2014 | Ho et al. | 128/206.21 |
| 8,807,135 B2 | 8/2014 | Worboys et al. | 128/206.24 |
| 8,813,748 B2 | 8/2014 | Kwok et al. | 128/206.24 |
| 8,881,728 B2 | 11/2014 | Sher et al. | 128/205.25 |
| 8,915,861 B2 | 12/2014 | Yamamori et al. | 600/532 |
| 8,939,151 B2 | 1/2015 | McAuley et al. | 128/205.25 |
| 8,944,061 B2 | 2/2015 | D'Souza et al. | 128/206.24 |
| D726,303 S | 4/2015 | Rollins | D24/110.1 |
| 9,010,330 B2 | 4/2015 | Barlow et al. | 128/201.18 |
| 9,010,331 B2 | 4/2015 | Lang et al. | A61M 16/06 |
| 9,022,029 B2 | 5/2015 | Varga et al. | A61B 5/0836 |
| 9,027,556 B2 | 5/2015 | Ng et al. | 128/205.25 |
| 9,138,169 B2 | 9/2015 | Beard | A61B 5/097 |
| 9,186,474 B1 | 11/2015 | Rollins | |
| 9,295,799 B2 | 3/2016 | McAuley et al. | A61M 16/06 |
| 9,295,800 B2 | 3/2016 | Davidson et al. | A61M 16/06 |
| D753,287 S | 4/2016 | Darab | D24/110.4 |
| D753,816 S | 4/2016 | Darab | D24/110.4 |
| 9,375,545 B2 | 6/2016 | Darkin et al. | A61M 16/0683 |
| 2002/0074001 A1 | 6/2002 | Kwok et al. | |
| 2002/0174868 A1 | 11/2002 | Kwok et al. | 128/205.25 |
| 2003/0024533 A1 | 2/2003 | Sniadach | 128/205.25 |
| 2003/0047189 A1 | 3/2003 | Kumar et al. | |
| 2003/0145859 A1 | 8/2003 | Bohn et al. | 128/206.24 |
| 2003/0183232 A1 | 10/2003 | Fukunaga et al. | 128/204.18 |
| 2004/0035423 A1 | 2/2004 | Platt et al. | |
| 2004/0069306 A1 | 4/2004 | Moenning | 128/207.13 |
| 2004/0221850 A1 | 11/2004 | Ging et al. | 128/206.27 |
| 2005/0028811 A1 | 2/2005 | Nelson et al. | 128/200.11 |
| 2005/0051168 A1 | 3/2005 | DeVries et al. | |
| 2005/0145247 A1* | 7/2005 | Nashed | A61M 16/00 128/204.18 |
| 2005/0160532 A1 | 7/2005 | Froelich | 5/637 |
| 2005/0193493 A1 | 9/2005 | Gabbay | 5/644 |
| 2006/0032500 A1 | 2/2006 | Ghiron et al. | 128/202.27 |
| 2006/0042631 A1 | 3/2006 | Martin et al. | 128/207.18 |
| 2006/0118117 A1 | 6/2006 | Berthon-Jones et al. | 128/206.21 |
| 2006/0124131 A1 | 6/2006 | Chandran et al. | |
| 2006/0168730 A1 | 8/2006 | Menkedick et al. | 5/618 |
| 2006/0174889 A1 | 8/2006 | Noble | 128/206.11 |
| 2006/0231091 A1 | 10/2006 | Camarillo | 128/200.21 |
| 2007/0000495 A1* | 1/2007 | Matula, Jr. | A62B 18/084 128/207.18 |
| 2007/0062536 A1 | 3/2007 | McAuley et al. | 128/206.21 |
| 2007/0113847 A1 | 5/2007 | Acker et al. | 128/204.18 |
| 2007/0113856 A1 | 5/2007 | Acker et al. | 128/207.14 |
| 2007/0267017 A1 | 11/2007 | McAuley et al. | 128/204.18 |
| 2007/0271699 A1 | 11/2007 | Sacchetti | 5/495 |
| 2007/0295335 A1 | 12/2007 | Nashed | 128/206.24 |
| 2008/0006276 A1 | 1/2008 | Kreutzmann et al. | |
| 2008/0053446 A1 | 3/2008 | Sleeper et al. | 128/205.25 |
| 2008/0092898 A1 | 4/2008 | Schneider et al. | 128/206.28 |
| 2008/0196715 A1 | 8/2008 | Yamamori | 128/203.12 |
| 2008/0221470 A1 | 9/2008 | Sather et al. | 600/533 |
| 2008/0230067 A1 | 9/2008 | Kwok et al. | 128/206.24 |
| 2008/0275357 A1 | 11/2008 | Porat et al. | |
| 2009/0084385 A1 | 4/2009 | Lang | 128/206.21 |
| 2009/0114229 A1 | 5/2009 | Frater et al. | 128/206.24 |
| 2009/0114230 A1 | 5/2009 | Hernandez et al. | 128/206.24 |
| 2009/0133696 A1 | 5/2009 | Remmers et al. | 128/204.26 |
| 2009/0178680 A1 | 7/2009 | Chang | 128/206.21 |
| 2009/0250061 A1 | 10/2009 | Marasigan | 128/205.13 |
| 2009/0260628 A1 | 10/2009 | Flynn | 128/203.28 |
| 2009/0275851 A1 | 11/2009 | Colman et al. | |
| 2009/0301472 A1 | 12/2009 | Kim et al. | 128/200.16 |
| 2009/0320850 A1 | 12/2009 | Wallnewitz et al. | 128/207.11 |
| 2010/0122701 A1 | 5/2010 | Gunaratnam | |
| 2010/0122704 A1* | 5/2010 | Moenning, Jr. | A61M 16/06 128/206.24 |
| 2010/0122705 A1 | 5/2010 | Moenning, Jr. | |
| 2010/0147313 A1 | 6/2010 | Albrecht | 128/845 |
| 2010/0170513 A1 | 7/2010 | Bowditch | 128/204.23 |
| 2010/0170516 A1 | 7/2010 | Grane | |
| 2010/0218316 A1 | 9/2010 | Nissen et al. | 5/632 |
| 2010/0224199 A1 | 9/2010 | Smith et al. | 128/863 |
| 2010/0275919 A1 | 11/2010 | Sung | 128/204.22 |
| 2010/0313891 A1 | 12/2010 | Veliss et al. | |
| 2011/0054366 A1 | 3/2011 | Smith et al. | 601/15 |
| 2011/0072582 A1 | 3/2011 | Patterson et al. | 5/484 |
| 2011/0083670 A1 | 4/2011 | Walacavage | 128/205.12 |
| 2011/0092930 A1 | 4/2011 | Poorman | 604/356 |
| 2011/0108035 A1 | 5/2011 | Samaniego | 128/206.17 |
| 2011/0114099 A1 | 5/2011 | Goldstein | 128/848 |
| 2011/0155136 A1 | 6/2011 | Lee | 128/205.24 |
| 2011/0173750 A1 | 7/2011 | Lehmann | 5/486 |
| 2011/0186050 A1 | 8/2011 | Daly | 128/204.23 |
| 2011/0214674 A1 | 9/2011 | Ging et al. | 128/206.21 |
| 2011/0253150 A1 | 10/2011 | King | 128/845 |
| 2011/0265796 A1 | 11/2011 | Amarasinghe et al. | 128/206.28 |
| 2011/0290253 A1 | 12/2011 | McAuley et al. | 128/205.25 |
| 2012/0080035 A1 | 4/2012 | Guney et al. | 128/205.25 |
| 2012/0111330 A1 | 5/2012 | Gartner | 128/205.23 |
| 2012/0144588 A1 | 6/2012 | Heimbrock et al. | 5/624 |
| 2012/0180220 A1 | 7/2012 | Popitz | 5/638 |
| 2012/0222680 A1 | 9/2012 | Eves et al. | 128/206.24 |
| 2012/0227736 A1 | 9/2012 | Bowsher | 128/202.27 |
| 2012/0234263 A1 | 9/2012 | Mazzone et al. | 128/206.26 |
| 2012/0247475 A1 | 10/2012 | Hernandez et al. | |
| 2012/0285455 A1 | 11/2012 | Varga et al. | 128/204.21 |
| 2012/0285466 A1 | 11/2012 | Pierro et al. | 128/206.24 |
| 2013/0014760 A1 | 1/2013 | Matula, Jr. et al. | 128/205.25 |
| 2013/0023729 A1 | 1/2013 | Vazales | |
| 2013/0060157 A1 | 3/2013 | Beard | 600/532 |
| 2013/0109992 A1 | 5/2013 | Guyette | 600/532 |
| 2013/0146060 A1 | 6/2013 | Ho et al. | 128/205.25 |
| 2013/0186413 A1 | 7/2013 | Haines et al. | 128/854 |
| 2013/0190643 A1 | 7/2013 | Brambilla | A61M 16/0875 |
| 2013/0192601 A1 | 8/2013 | Reischl et al. | 128/205.25 |
| 2013/0192602 A1 | 8/2013 | Leibitzki et al. | 128/205.27 |
| 2013/0199537 A1 | 8/2013 | Formica et al. | A61M 16/0666 |
| 2013/0319417 A1 | 12/2013 | Weinman | 128/205.25 |
| 2014/0076411 A1 | 3/2014 | Darab | 128/203.12 |
| 2014/0083425 A1 | 3/2014 | Moenning | 128/203.29 |
| 2014/0144448 A1 | 5/2014 | Eifler | 128/206.24 |
| 2014/0158135 A1 | 6/2014 | Shyong | 128/206.21 |
| 2014/0158136 A1 | 6/2014 | Romagnoli et al. | 128/206.24 |
| 2014/0215687 A1 | 8/2014 | Andrews | 2/170 |
| 2014/0243600 A1 | 8/2014 | Eisenberger | 600/114 |
| 2014/0245537 A1 | 9/2014 | Allen | 5/622 |
| 2014/0251333 A1 | 9/2014 | Burk | 128/205.12 |
| 2014/0326246 A1 | 11/2014 | Chodkowski et al. | 128/206.24 |
| 2014/0352072 A1 | 12/2014 | Holladay | 5/655.5 |
| 2014/0360504 A1 | 12/2014 | Kwok | A61M 16/0605 |
| 2015/0047647 A1 | 2/2015 | Winer | 128/854 |
| 2015/0059759 A1 | 3/2015 | Frater et al. | 128/205.25 |
| 2015/0144140 A1 | 5/2015 | Eury | A61M 16/0622 |
| 2015/0217075 A1 | 8/2015 | Nair | 600/531 |
| 2015/0238716 A1 | 8/2015 | Budhiraja et al. | A61M 16/0003 |
| 2015/0250970 A1 | 9/2015 | Bowsher | A61M 16/0616 |
| 2015/0250971 A1 | 9/2015 | Bachelder et al. | A61M 16/0616 |
| 2015/0273170 A1 | 10/2015 | Bachelder et al. | A61M 16/0616 |
| 2015/0273171 A1 | 10/2015 | Sullivan et al. | A61M 16/0683 |
| 2015/0335852 A1 | 11/2015 | Miller | A61M 16/208 |
| 2016/0015923 A1 | 1/2016 | Chodkowski et al. | A61M 16/0622 |
| 2016/0022944 A1 | 1/2016 | Chodkowski et al. | A61M 16/0616 |
| 2016/0038709 A1 | 2/2016 | Beard | 128/205.12 |
| 2016/0067441 A1 | 3/2016 | Bearne et al. | A61M 16/0683 |
| 2016/0184540 A1 | 6/2016 | Kokko | A61M 16/0069 |
| 2016/0213281 A1* | 7/2016 | Eckerbom | B29C 45/44 |

(56) References Cited

U.S. PATENT DOCUMENTS

| | | | |
|---|---|---|---|
| 2016/0213871 A1 | 7/2016 | Darab | |
| 2016/0279368 A1 | 9/2016 | Isenberg | ............ A61M 16/0605 |

FOREIGN PATENT DOCUMENTS

| | | | | |
|---|---|---|---|---|
| CN | 201643308 U | 11/2010 | | |
| CN | 101954138 A | 1/2011 | | |
| CN | 202478364 | 10/2012 | ............ | A61M 16/06 |
| CN | 202505937 | 10/2012 | ............ | A61M 16/06 |
| CN | 103153378 A | 6/2013 | | |
| CN | 203724588 U | 7/2014 | | |
| CN | 204275233 U | 4/2015 | | |
| DE | 19947722 | 4/2001 | ............ | A61M 16/06 |
| EP | 2433666 | 3/2012 | ............ | A61M 16/06 |
| GB | 187863 | 11/1922 | | |
| GB | 2209950 A | 6/1989 | | |
| GB | 2456136 | 7/2009 | | |
| JP | 2005318975 A | 11/2005 | | |
| JP | 2008511399 A | 4/2008 | | |
| JP | 2008200061 A | 9/2008 | | |
| JP | 2011036643 A | 2/2011 | | |
| JP | 2013517016 A | 5/2013 | | |
| TW | 201231105 A | 8/2012 | | |
| WO | WO2010059592 | 5/2010 | ............ | A61M 16/06 |
| WO | WO-2012006415 A1 | 1/2012 | | |
| WO | WO-2012106373 A2 | 8/2012 | | |
| WO | WO2013036839 | 3/2013 | ............ | A61M 16/06 |
| WO | WO2013/064950 | 5/2013 | ............ | A61M 16/06 |
| WO | WO-2013142909 A1 | 10/2013 | | |
| WO | WO-2013171617 A2 | 11/2013 | | |
| WO | WO2014038959 | 3/2014 | ............ | A61M 16/00 |
| WO | WO2014210606 | 12/2014 | ............ | A61G 13/02 |
| WO | WO2015063283 | 5/2015 | ............ | A61M 16/06 |
| WO | WO2015131262 | 9/2015 | ............ | A61M 16/06 |
| WO | WO2015147947 | 10/2015 | ............ | A61M 15/06 |
| WO | WO2015187995 | 12/2015 | ............ | A61M 16/06 |
| WO | WO2016007749 | 1/2016 | ............ | A61M 16/10 |
| WO | WO2016097948 | 6/2016 | ............ | A61M 16/06 |

OTHER PUBLICATIONS

Chinese First Notification to Make Rectification issued in application No. 201730161613.8, dated Aug. 7, 2017 (2 pgs).
Chinese Notification of Grant issued in application No. 201530191921.6, dated Feb. 15, 2016 (12 pgs).
Chinese Second Notification to Make Rectification issued in application No. 201730161613.8, dated Sep. 19, 2017 (11 pgs).
Chinese Second Office Action issued in application No. 201480042735.9, dated Nov. 6, 2017 (21 pgs).
European Examination Report issued in application 003933217-0001, dated May 16, 2017 (2 pgs).
International Preliminary Report on Patentability issued in application No. PCT/US2016/037070, dated Dec. 12, 2017 (7 pgs).
International Search Report and Written Opinion issued in application No. PCT/US2017/048046, dated Nov. 6, 2017 (11 pgs).
Japanese Certified Decision for Registration issued in application No. 2016-005262, dated Dec. 22, 2017 (4 pgs).
Japanese Certified Decision for Registration issued in application No. 2016-005263, dated Dec. 22, 2017 (4 pgs).
Japanese Decision for Registration issued in application No. 2017-009813, dated Oct. 6, 2017 (2 pgs).
Japanese Office Action issued in application No. 2017-009813, dated Jul. 20, 2017 (3 pgs).
Notice of Allowance (Corrected) issued in U.S. Appl. No. 15/288,973, dated Mar. 10, 2017 (9 pgs).
Notice of Allowance (Corrected) issued in U.S. Appl. No. 15/288,973, dated Mar. 24, 2017 (9 pgs).
Notice of Allowance (Corrected) issued in U.S. Appl. No. 15/288,973, dated Feb. 10, 2017 (16 pgs).
Office Action issued in U.S. Appl. No. 15/272,074, dated Jul. 31, 2017 (34 pgs).
Office Action issued in U.S. Appl. No. 15/272,074, dated Sep. 13, 2017 (5 pgs).
Office Action issued in U.S. Appl. No. 15/272,160, dated Dec. 15, 2017 (34 pgs).
Office Action issued in U.S. Appl. No. 15/272,190, dated Dec. 28, 2017 (22 pgs).
Office Action issued in U.S. Appl. No. 15/272,190, dated Jun. 21, 2017 (7 pgs).
Office Action issued in U.S. Appl. No. 29/520,420, dated Dec. 8, 2017 (5 pgs).
Office Action issued in U.S. Appl. No. 29/530,124 dated Aug. 9, 2017 (11 pgs).
Office Action issued in U.S. Appl. No. 29/530,124, dated Aug. 30, 2017 (3 pgs).
Office Action issued in U.S. Appl. No. 29/530,124, dated Jun. 21, 2017 (14 pgs).
Office Action issued in U.S. Appl. No. 29/530,124, dated Nov. 29, 2017 (31 pgs).
Singapore Invitation to Respond to Written Opinion issued in application No. 11201610048P, dated Sep. 19, 2017 (16 pgs).
Singapore Invitation to Respond to Written Opinion issued in application No. 11201701253U, dated Nov. 8, 2017 (12 pgs).
Extended European Search Report for Application No. 16808466.3, dated Jun. 13, 2019, 13 pages.
Chinese Office Action for Application No. 201580029981.5, dated Sep. 5, 2018, 14 pages.
Extended European Search Report for Application No. 15803670.7, dated Oct. 24, 2018, 12 pages.
Extended European Search Report for Application No. 15833101.7, dated Jul. 3, 2018, 13 pages.
Japanese Office Action for Application No. 2017-509724, dated Jul. 24, 2018, 7 pages.
International Search Report and Written Opinion issued in application No. PCT/US2016/037070, dated Nov. 10, 2016 (11 pgs).
Japanese Office Action (w/translation) issued in application No. 2016-006559, dated Aug. 29, 2016 (3 pgs).
Japanese Office Action (w/translation) issued in application No. 2016-006560, dated Aug. 29, 2016 (3 pgs).
Australian Certificate of Registration issued in application No. 201512961, dated Aug. 10, 2015 (5 pgs).
Australian Certificate of Registration issued in application No. 201512962, dated Aug. 12, 2015 (5 pgs).
Ball et al., "Performance comparison of two anaesthetic facemasks," Anaesth Intensive Care, Apr. 2007, vol. 35, issue 2, 226-9 (abstract only) (2 pgs).
Canadian Office Action issued in application No. 162891, dated Apr. 5, 2016 (1 pg).
Canadian Office Action issued in application No. 162891, dated Nov. 10, 2015 (7 pgs).
CPAP product description, http://www.cpap.com/productpage/pr-amara-full-face-cpap-mask-gel-silicone.html, downloaded Jul. 28, 2016, 11 pages.
CPAPXCHANGE product image, http://www.cpapxchange.com/cpap-masks-bipap-masks/bluegel-full-cushion-comfortgel-cpap-bipap-masks.jpg, downloaded Jul. 28, 2016, 1 page.
DirectHome Medical product description, http://www.directhomemedical.com/profilelite-gel-cpap-mask-philipsrespironics.html#.VwXLIPkrLIU, downloaded Jul. 28, 2016, 6 pages.
Indian Office Action issued in related Indian Design Patent Application Serial No. 272704, dated Aug. 28, 2015 (13 pgs).
InnoMed Technologies Hybrid mask product description, http://innomedinc.com/hybrid/, downloaded Jul. 28, 2016, 4 pages.
InnoMed Technologies Svlent mask product description, http://innomedinc.com/sylent-ne-disposable-nasal-mask/, downloaded Jul. 28, 2016, 2 pages.
International Preliminary Report on Patentability issued in application No. PCT/US14/44934, dated Jan. 7, 2016 (12 pgs).
International Preliminary Report on Patentability issued in application No. PCT/US2105/021323, dated Oct. 6, 2016 (8 pgs).
International Search Report and Written Opinion issued in application No. PCT/US2015/044341, dated Jan. 7, 2016 (13 pgs).
International Search Report and Written Opinion issued in application No. PCT/US2015/34277, dated Nov. 23, 2015 (17 pgs).

(56) References Cited

OTHER PUBLICATIONS

International Search Report issued in application No. PCT/US14/44934, dated Jan. 2, 2015 (16 pgs).
Invitation to Pay Additional Fees issued in application No. PCT/US15/44341, dated Oct. 21, 2015 (2 pgs).
Invitation to Pay Additional Fees issued in application No. PCT/US14/44934, dated Oct. 24, 2014 (3 pgs).
Israeli Notice of Allowance issued in application No. 57056 (no translation), dated May 29, 2016 (1 pg).
Israeli Office Action issued in application No. 57056 (w/translation of relevant portions), dated Nov. 1, 2015 (3 pgs).
Israeli Office Action issued in application No. 57850 (w/translation of relevant portions), dated Feb. 15, 2016 (3 pgs).
Israeli Office Action issued in application No. 57850 (w/translation of relevant portions), dated Jun. 30, 2016 (2 pgs).
Israeli Office Action issued in application No. 57850 (w/translation of relevant portions), dated Jul. 19, 2016 (3 pgs).
Japanese Office Action issued in application No. 2015-013148, dated Dec. 4, 2015 (3 pgs).
Japanese Office Action issued in application No. 2016-005262, dated Jun. 30, 2016 (1 pg).
Japanese Office Action issued in application No. 2016-005263, dated Jun. 30, 2016 (1 pg).
Korean Design of Registration issued in Korean related Application Serial No. 30-2015-0029561, M001 (w/translation), dated Jun. 29, 2016 (3 pgs).
Korean Design of Registration issued in Korean related Application Serial No. 30-2015-0029561, M002 (w/translation), dated Jun. 27, 2016 (3 pgs).
Korean Office Action issued in application No. 30-2015-0029561, M002 (w/translation), dated May 23, 2016 (6 pgs).
Korean Office Action issued in application No. 30-2015-0029561, M001, dated May 23, 2016 (2 pgs).
Korean Office Action issued in application No. 30-2015-0029561, M002 (w/translation), dated Dec. 24, 2015 (7 pgs).
Korean Office Action issued in application No. 30-2015-0029561, M001 (w/translation), dated Dec. 24, 2015 (12 pgs).
Korean Office Action issued in application No. 30-2015-0029561, M001, dated Jun. 9, 2016 (16 pgs).
Korean Office Action issued in application No. 30-2015-0029561, M002, dated Jun. 9, 2016 (3 pgs).
Liang, Yafen et al., "Nasal Ventilation is More Effective than Combined Oral-Nasal Ventilation during Induction of General Anesthesia in Adult Subjects", Anesthesiology 2008, vol. 108, No. 6, Jun. 2008, pp. 998-1003.
Office Action issued in U.S. Appl. No. 29/530,124, dated Aug. 12, 2016 (17 pgs).
Office Action issued in related Design U.S. Appl. No. 29/520,420, dated Aug. 11, 2016 (18 pgs).
Sleep Medicine Solutions product description, http://sleepmedicinesolutions.net.au/cpap-spare-parts/26-fisher-paykel-zest-foams.html, downloaded Jul. 28, 2016, 2 pages.
Sleepnet homenage. https://web.archive.org/web/20111031122613/http://www.sleepnetmasks.com/, downloaded Jul. 28, 2016, 4 pages.
European Supplementary Partial European Search Report for application No. 14818563.0, dated Jan. 30, 2017 (6 pages).
Notice of Allowance issued in U.S. Appl. No. 15/288,973, dated Feb. 1, 2017 (25 pgs).
Notice of Decision of Registration for Design issued in Korean Design Application 30-20016-0014111, dated Dec. 13, 2016 (3 pages with translation).
Office Action Issued in U.S. Appl. No. 15/272,160, dated Jan. 4, 2017 (31 pgs).
Office Action issued in U.S. Appl. No. 15/272,190, dated Jan. 30, 2017 (32 pgs).
Office Action issued in U.S. Appl. No. 15/288,973, dated Dec. 14, 2016 (21 pgs).
Preliminary Report on Patentability issued in application No. PCT/US2015/034277, dated Dec. 15, 2016 (11 pgs).

Singapore Search Report issued in application 11201510589, dated Jan. 31, 2017 (11 pgs).
International Preliminary Report on Patentability issued in application No. PCT/US2015/044341, dated Mar. 2, 2017 (10 pgs).
Office Action issued in U.S. Appl. No. 15/272,074, dated Apr. 19, 2017 (54 pgs).
Office Action issued in U.S. Appl. No. 15/272,160, dated Apr. 24, 2017 (39 pgs).
Office Action issued in U.S. Appl. No. 29/520,420, dated Apr. 7, 2017 (3 pgs).
Office Action issued in U.S. Appl. No. 29/520,420, dated Feb. 24, 2017 (14 pgs).
Office Action issued in U.S. Appl. No. 29/530,124, dated Apr. 19, 2017 (6 pgs).
Office Action issued in U.S. Appl. No. 29/530,124, dated Feb. 28, 2017 (16 pgs).
U.S. Appl. No. 29/511,716, filed Dec. 12, 2014.
U.S. Appl. No. 29/520,420, filed Mar. 13, 2015.
U.S. Appl. No. 29/530,124, filed Jun. 12, 2015.
U.S. Appl. No. 14/901,647, filed Dec. 28, 2015.
U.S. Appl. No. 15/217,753, filed Jul. 22, 2016.
U.S. Appl. No. 15/127,758, filed Sep. 20, 2016.
U.S. Appl. No. 15/127,760, filed Sep. 20, 2016.
U.S. Appl. No. 15/272,074, filed Sep. 21, 2016.
U.S. Appl. No. 15/272,160, filed Sep. 21, 2016.
U.S. Appl. No. 15/272,190, filed Sep. 21, 2016.
U.S. Appl. No. 15/288,973, filed Oct. 7, 2016.
U.S. Appl. No. 15/510,469, filed Mar. 10, 2017.
Chinese First Office Action issued in application No. 201480042735.9 dated Apr. 5, 2017 (w/ translation) (18 pgs).
Extended European Search Report issued in application No. 14818563.0-1651 dated May 3, 2017 (12 pgs).
Japanese Decision for Registration issued in application on. 2016-006559, dated May 12, 2017 (w/ translation) (2 pgs).
Japanese Decision for Registration issued in application on. 2016-006560, dated May 12, 2017 (w/ translation) (2 pgs).
Japanese Office Action (w/translation) issued in application 2016-005263, dated Apr. 28, 2017 (7 pgs).
Japanese Office Action (w/translation) issued in application 2016-005262, dated Apr. 28, 2017 (7 pgs).
Office Action issued in U.S. Appl. No. 15/272,190, dated May 23, 2017 (36 pgs).
Office Action issued in U.S. Appl. No. 29/520,420, dated Jun. 15, 2017 (12 pgs).
Australian Office Action for Application No. 2016275127, dated Apr. 20, 2020, 5 pages.
Japanese Office Action for Application No. 2017-564038, dated Mar. 17, 2019, 9 pages.
European Office Action for Application No. 16808466.3, dated May 7, 2020, 4 pages.
Japanese Office Action for Application No. 2017-564038, dated Jun. 30, 2020, 14 pages.
Chinese Office Action for Application No. 201680034083.3, dated Jul. 9, 2020, 9 pages.
Chinese Office Action for Application No. 201680034083.3, dated Dec. 26, 2019, 11 pages.
Japanese Office Action for Application No. 2017564038, dated Oct. 13, 2020, 6 pages.
Chinese Office Action for Application No. 201680034083.3, dated Jun. 18, 2021, 9 pages including translation.
Canadian Office Action for Application No. 2988785, dated May 31, 2021, 6 pages.
Extended European Search Report for Application No. 21186150.5, dated Oct. 28, 2021, 8 pages.
Chinese Office Action for Application No. 201680034083.3, dated Oct. 18, 2021, 7 pages including translation.
Chinese Office Action for Application No. 201680034083.3, dated Mar. 25, 2021, 17 pages including translation.
Chinese Office Action for Application No. 201680034083.3, dated Dec. 14, 2020, 11 pages including English translation.
Canadian Office Action for Application No. 2988785, dated Mar. 3, 2022, 4 pages.

(56) References Cited

OTHER PUBLICATIONS

Japanese Office Action for Application No. 2021-032508, dated Jan. 5, 2022, 6 pages including translation.

* cited by examiner

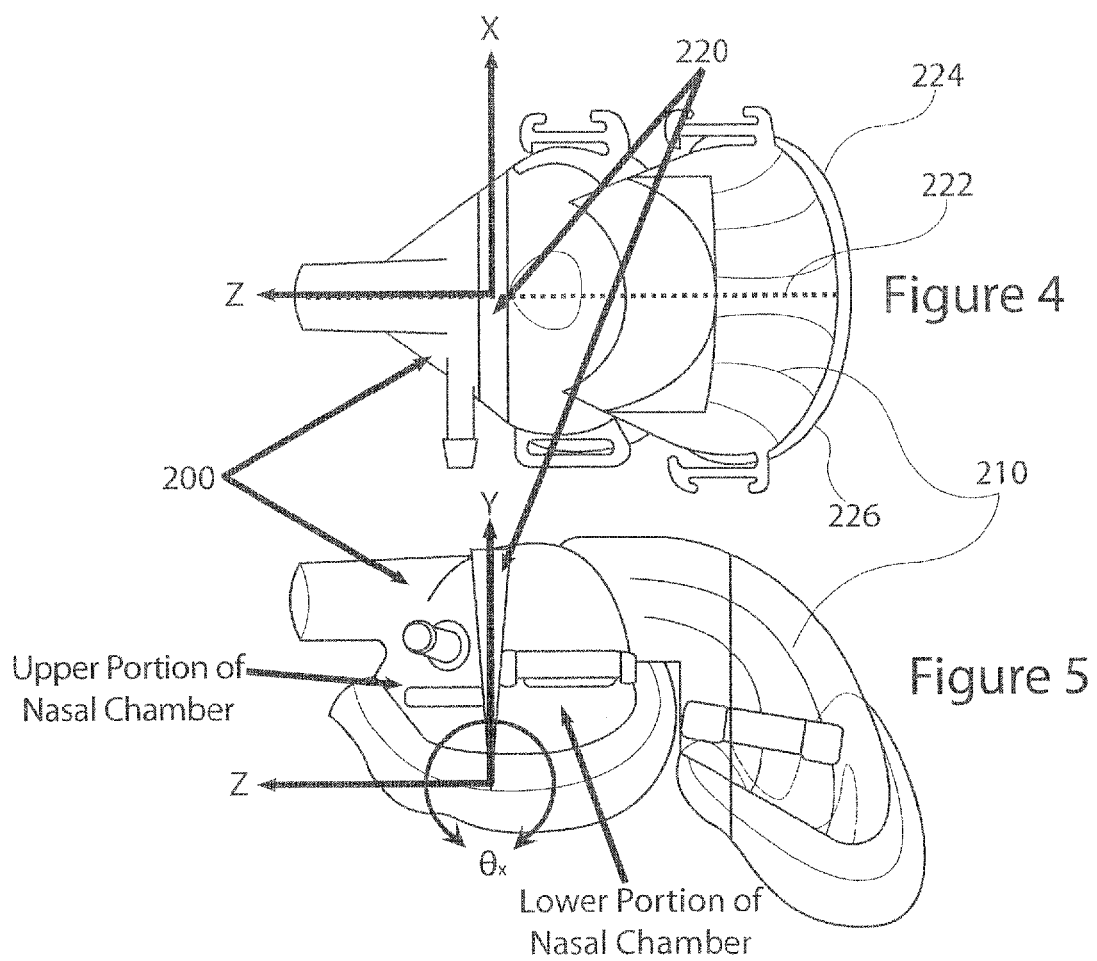

Section A-A

Section B-B

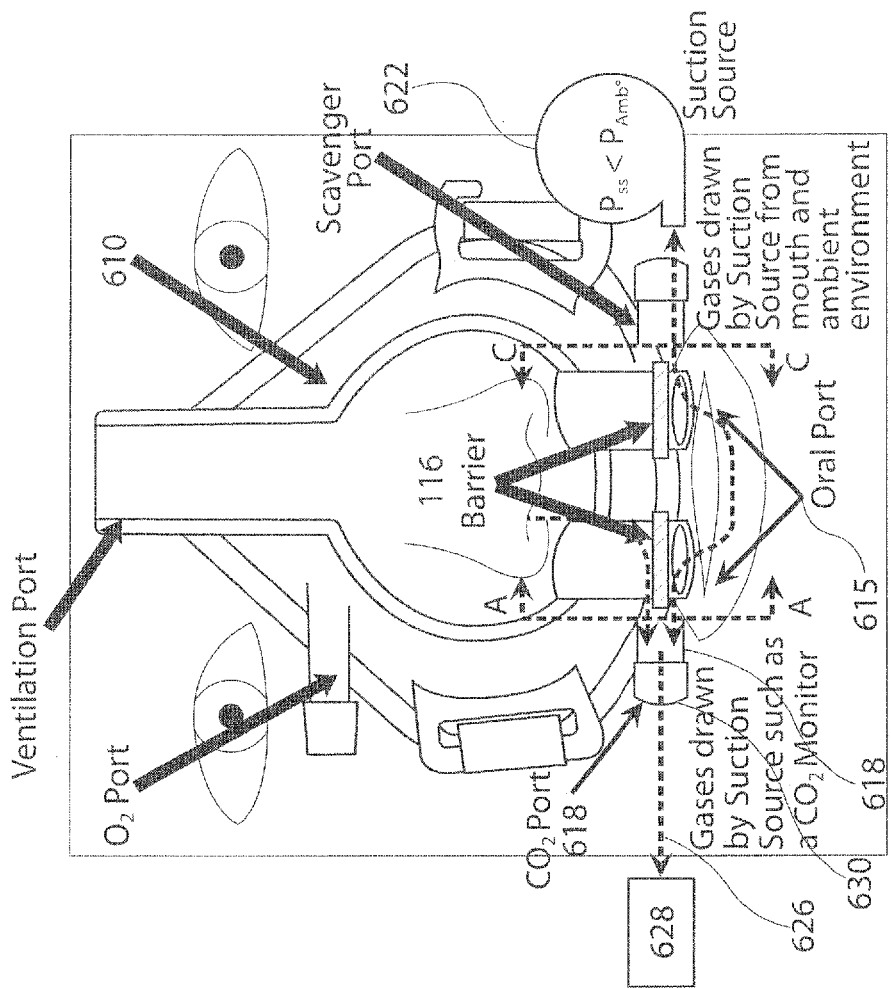
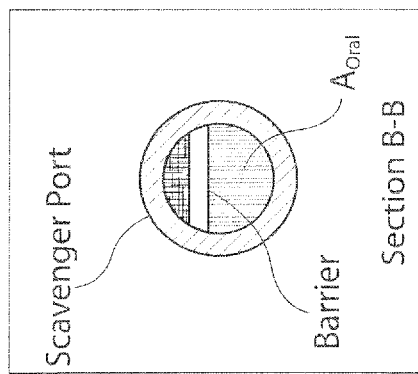
Figure 15A
Figure 15B

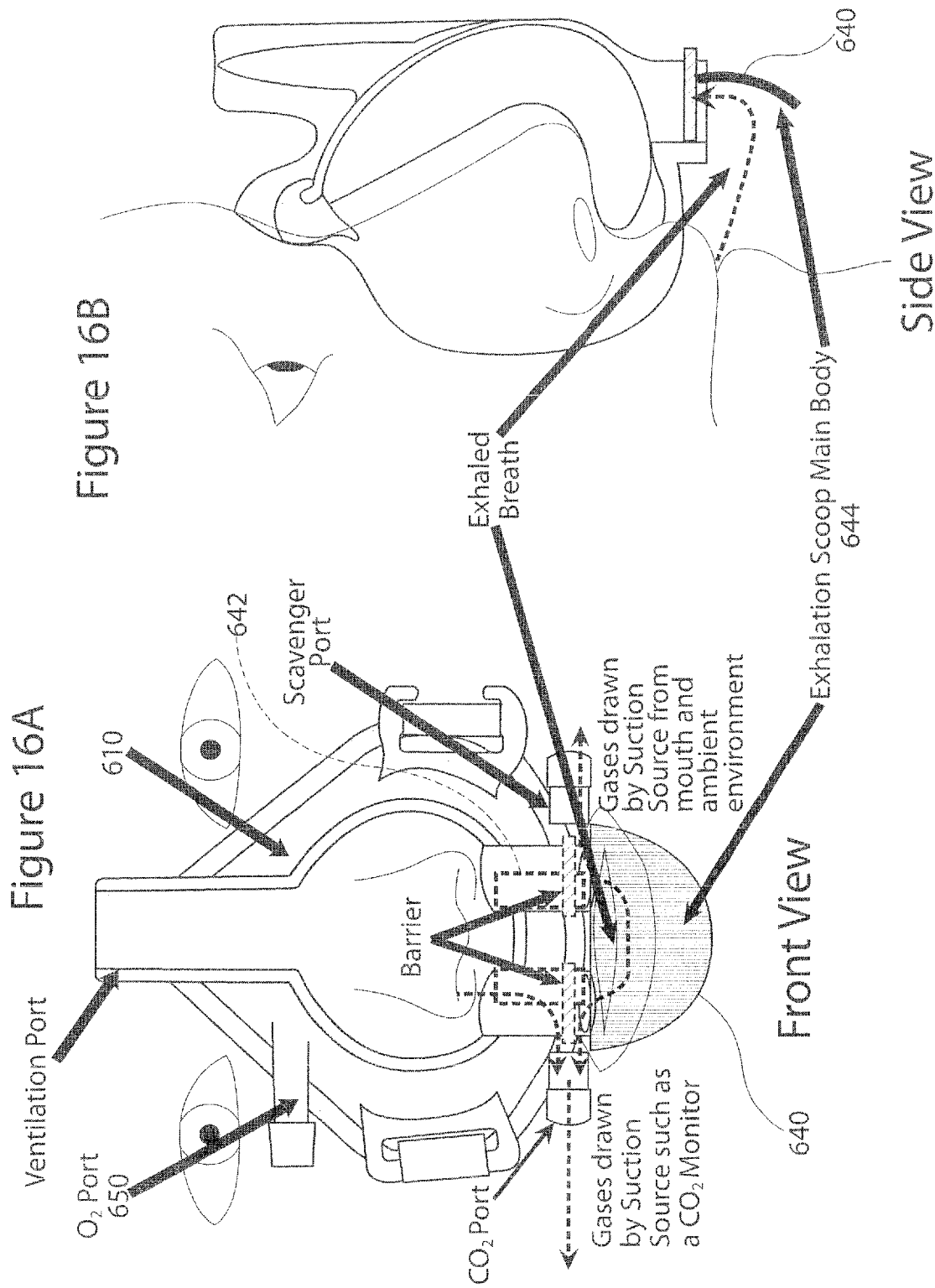

VENTILATION MASK

The present invention relates to improvements in anesthesia masks and masks.

During surgery a patient usually is placed under anesthesia. The most common delivery system consists of canisters containing anesthesia gases and oxygen, a system of regulating the gas flow and the patient's breathing, and a device ensuring the potency of the patient's airway for breathing, oxygenation and the delivery of the anesthetic gas mixture. A ventilation mask is used to provide oxygen to the patient either during emergency and/or elective airway management, which includes but is not limited to: before a patient is anesthetized for surgery; while the patient is sedated during the surgery or procedure; while the patient is recovering from anesthesia; after the patient has recovered from anesthesia; and during any event where a patient requires supplemental oxygen. However, conventional ventilation masks are less then ideal.

Moreover, situations may arise during surgery that require rapid intubation of a patient. Full face masks, i.e. masks covering both the nose and mouth of a patient are problematic in emergency situations since a mask must be removed to uncover the mouth of a patient for intubation. However, removing the mask also removes oxygen support.

In our co-pending PCT Application Serial Nos. PCT/US2014/44934, PCT/US2015/034277 and PCT/US2015/044341 (hereinafter the '934, '277 and '341 PCT applications), we provide improved ventilation/anesthesia masks that overcome the aforesaid and other problems with the prior art by providing, in one aspect, a combination mask comprising a nasal portion or mask and an oral portion or mask defining respectively a nasal chamber and an oral chamber, detachably connected to one another wherein the nasal mask may be used separately or connected to the oral mask as a combination nasal/oral mask. We also provide the nasal mask with one or more ports, and various strap systems for holding the mask on a patient's face. Such combination nasal/oral masks are available commercially from Revolutionary Medical Devices, Inc. of Tucson, Ariz., under the trademark SuperNO$_2$VA®.

The present invention in one aspect provides nasal ventilation mask having one or more attachment ports located adjacent to and overlying an upper lip of a patient when worn. Preferably the attachment ports are sealable by a self-closing valve, preferably a duckbill valve, a frangible membrane, a plug or a cap, and are adapted to support a functional accessory. In a preferred embodiment the functional accessory comprises a sensor adapted to monitor one or more of the following parameters selected from the group consisting of $CO_2$ concentration, $O_2$ concentration, N concentration, anesthesia gas concentration, pressure, relative humidity, temperature and gas flow rate; an end-tidal $CO_2$ adaptor for monitoring end-tidal $CO_2$ from the nose and/or mouth of the wearer; or a sensor, a $CO_2$ scavenger, a gas collector or exhalation scoop, a nasal cannula, and/or an oral mask adapted to accommodate a functional device, preferably a laryngoscope a video laryngoscope, an endotracheal tube, a fiber optic bronchoscope, a rigid bronchoscope, a gastroenterology scope and/or suction tubing.

The present invention in another aspect provides a ventilation mask having upper and lower portions and/or left and right portions connected by an elastomeric hinge or bridge. In such aspect the mask maybe a full face mask, an oral mask, a nasal mask or a combination nasal/oral mask connected to one another. In such aspect the elastomeric hinge or bridge has an ability to rotate around the x and/or y and/or z direction. In a particularly preferred embodiment the mask comprises a combination nasal/oral mask in which the nasal portion of the mask and the oral portion of the mask are separable from one another.

The present invention in another aspect provides a nasal mask comprising an exhalation scoop mounted adjacent a lower portion of the mask positioned to overly an upper lip of a patient when the mask is worn, wherein the exhalation scoop is attached to the nasal mask through attachment ports that permit exhaled breath captured by the exhalation scoop to be diverted into the nasal mask, and a port for connection to a suction source.

The present invention in yet another aspect provides an anesthesia mask comprising a nasal mask adapted to seal to a patient's face when worn by a patient, and an exhaled breath scavenger attached to the mask adjacent its lower side which overlies an upper lip of a patient when the mask is worn by the patient. In such aspect the exhalation scoop or exhaled breath scavenger preferably is fixed to the mask by mechanical or adhesive attachments or brackets.

The present invention also provides a nasal mask comprising a generally triangularly-shaped frame having an apex forming a nasal bridge region connected by slanted side walls to a lip region, said nasal mask including a nasal bridge seal formed of an elastic membrane bridging the nasal bridge region and the side walls, and optionally including a lower lip seal formed of an elastic membrane bridging the lower lip region and adjacent portions of the side walls, for accommodating patient lips of various sizes and shapes, or in the alternative, only a lip seal formed of an elastic membrane bridging the lip region and the side walls.

In yet another aspect there is provided a breathing circuit for delivering oxygen and/or anesthetic gases through a mask to a patient, comprising a fresh gas supply line connected either directly to a mask or indirectly to the mask through a non-breathing circuit port, and an exhalation collecting tube connected between the non-breathing circuit port and a flexible reservoir bag, wherein the mask comprises a nasal ventilation mask, a full face mask with a valved connector or membrane seal, or a combined nasal/oral mask in which the oral mask is detachable. In such aspect, a first end of the fresh gas line preferably is either directly or indirectly connected to the mask, while a second end is connected to the fresh gas supply. Also, preferably the flexible reservoir bag defines a passageway for flow of gas in a first direction, said bag having a gas outlet and inlet, wherein the bag outlet is in communication with the exhalation collecting tube, which defines a passageway for flow of gas in a first and a second direction, wherein at least part of the walls of the bag preferably extend beyond sides of the exhalation collecting tube, and the first and second directions of gas flow are substantially parallel to, and laterally offset from, one another, and/or wherein the exhalation collecting tube is affixed to an outer surface of the reservoir bag.

Also provided by the present invention is a breathing circuit for delivering oxygen and/or anesthetic gases through a mask to a patient, wherein the mask comprises a full face mask, which includes a valved connector or membrane seal for maintaining positive pressure while simultaneously allowing passage of a functional tool into the mouth of a patient. In such embodiment, the functional tool may comprise, for example, a laryngoscope, a video laryngoscope, an endotracheal tube, a fiberoptic bronchoscope, a rigid bronchoscope, a gastroenterology endoscope, and/or suction tubing. Optionally included is a portable oxygen tank for transportation of the patient from one location to another, or connected to supplemental wall oxygen used in an operating room, or used in procedural room such as a GI suite, cardiac catheter lab, MRI, and bronchoscopy suite.

The present invention in another aspect provides a breathing circuit for delivering oxygen and/or anesthetic gases through a mask to a patient, wherein a fresh gas line is connected to a exhalation collecting tube, and the exhalation collecting tube is connected to a two chamber ventilation facemask, including an oral chamber and a nasal chamber, wherein the oral chamber is removable allowing the nasal chamber to stay on the patient for providing nasal CPAP and nasal NIPPV, while simultaneously allowing a surgeon access to the patient's mouth to perform a procedure.

In yet another aspect there is provided a breathing circuit for delivering oxygen and/or anesthetic gases through a mask to a patient, where a fresh gas line is connected to an exhalation collection tube, and an exhalation collecting tube is connected to a nasal mask for use in nasal CPAP and nasal NIPPV, said non-rebreathing breathing circuit further comprising a separate oral mask, having one or more ports which contain either one-way valved connectors or membrane seals that allow passage of a functional tool.

In such aspect the functional tool preferably comprises a video laryngoscope/laryngoscope, an endotracheal tube, and/or a fiberoptic bronchoscope with an endotracheal tube attached or a suction tool; the oral mask optionally preferably includes a port for scavenging gases; the exhalation collecting tube optionally preferably includes an end-tidal $CO_2$ port for connection to an end-tidal $CO_2$ monitor; and, the exhalation collecting tube optionally preferably includes-bacterial filters.

The present invention in yet another aspect provides a disposable CPAP mask having an exhaust optionally open to atmosphere, said mask being convertible from a nasal CPAP mask to a full face mask CPAP mask and vice versa. In such aspect, the nasal CPAP mask preferably comprises a nasal mask having a circuit port and an exhaust port, one or more attachment valves and an adaptor for connecting a PEEP valve and supplemental oxygen to the mask, optionally including a removable oral mask, and wherein the one or more attachment valves preferably comprise duck bill valves for engagement by proboscises of an oral chamber when attached to the nasal chamber.

Further features and advantages of the present invention will be seen from the following detailed description, taken in conjunction with the accompanying drawings, wherein:

FIG. 4 is a top plan view and FIG. 5 a side view of a hinged combination nasal/oral mask in accordance with an embodiment of the present invention;

FIGS. 15A and 15B are views similar to FIGS. 14A and 14C of still yet another embodiment of the present invention where an end tidal CO2 collector and gas scavenger are integrated as part of the Nasal chamber;

The present invention in one aspect is based on the realization that the nasal portion or mask of the combination nasal/oral mask as described in our aforesaid '934, '277 and '341 PCT applications, not only can be used separately as a nasal mask for nasal ventilation, but also as a platform for connecting other devices, attachments and accessories, to the nasal mask including other types of oral chambers for accommodating, for example, laryngoscopes, bronchoscopes, $CO_2$ scavengers, and adaptors and sensors for measuring, for example, $O_2$ or nitrogen concentrations, anesthesia gas concentration, end tidal $CO_2$, etc., as will described below.

However, before describing the other devices, attachments and accessories, we will describe various structural improvements to the nasal mask and the combination nasal/oral mask such as described in our aforesaid '934, '277 and '341 PCT applications.

Figure 1:
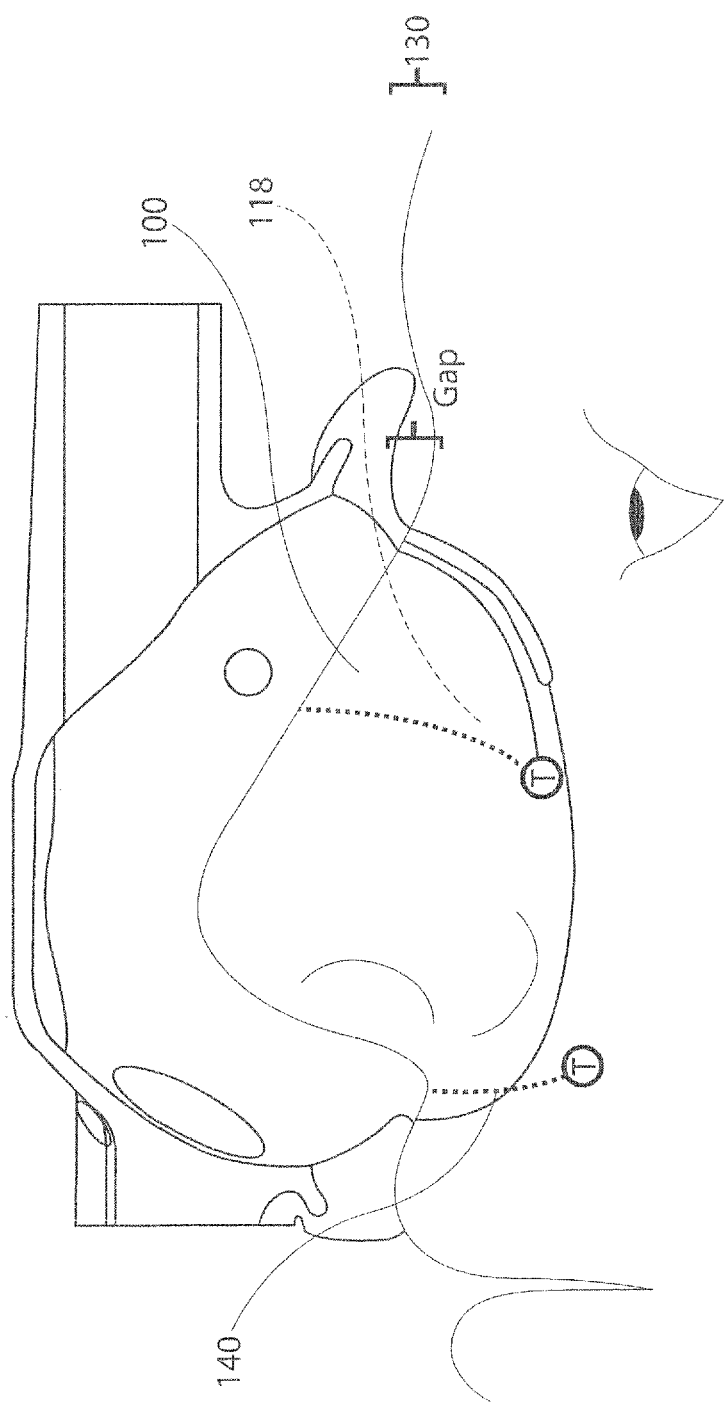
FIG. 1 is a side view of a nasal mask in accordance with one aspect of the present invention.
Figure 3:
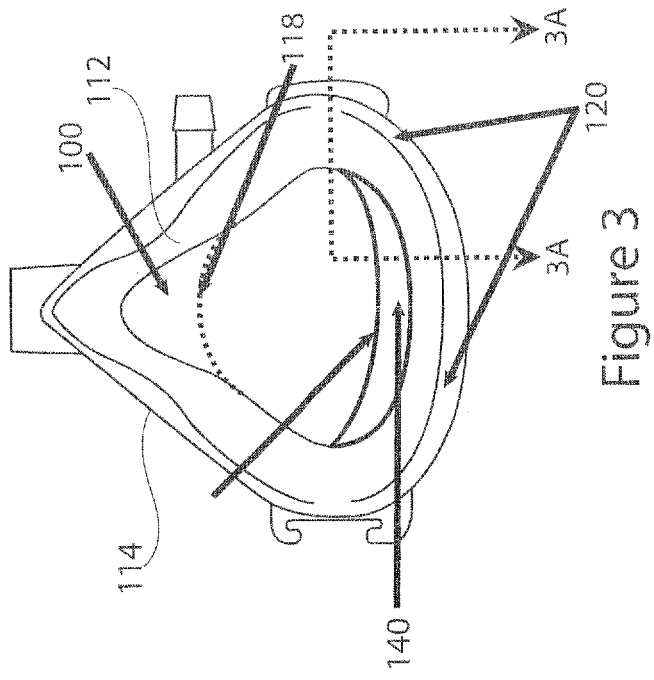
FIG. 3A is a cross-sectional view taken along line 3A-3A showing details of a Y-seal in accordance with a preferred embodiment of the invention.
Figure 2:
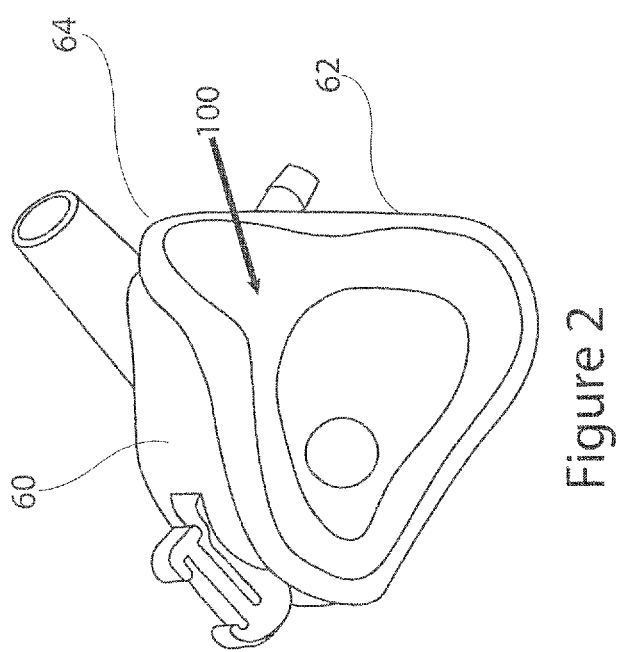
FIG. 2 is a perspective view and FIG. 3 a plan view from the inside of the mask of FIG. 1.
Figure 3A:
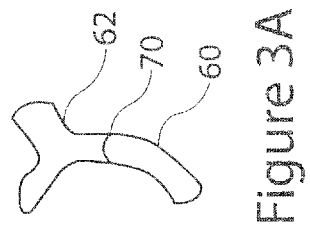

Referring to FIGS. 1-3, a nasal mask in accordance with the present invention provides a generally triangularly shaped shell having a relatively rigid body portion 60 formed of a transparent polymeric material. A multi-lobed, preferably Y-shaped seal 62 is fixed to rigid body 60 at 70. Seal 62 includes a nose bridge region 64 provided adjacent the "apex" area of triangularly shaped body 60. Seal 62 is formed of a resiliently deformable material preferably having a Shore A Hardness durometer of 2-10, more preferably 3-7, most preferably about 5. In order to provide a better seal for patients with different bridge heights and shapes, a nasal bridge seal in the form of an elastic membrane-like seal structure 100 is provided spanning the right side 112 and left side 114 of the mask terminating at the inside edge of seal 120. Seal 100 which preferably is formed integrally with seal 62, is thinned to a thickness of 0.04 to 9.7 mm, preferably 1 to 5 mm, most preferably about 2 mm. Being quite thin, and being formed of a resiliently deformable material, seal 100 readily deforms and stretches to intercept and conform to the nose of the patient. Thus, if there is a gap 130 at the top of the bridge as shown in FIG. 1, the clinician may slightly deform body 60 the nasal chamber (which is significantly more rigid than the elastic membrane 100), whereby to deform the elastic membrane-like nasal bridge seal, so that the edge of the nasal bridge seal 100 indicated by the dotted line 118 intercepts a lower portion of the patient's nose. Because seal 100 is attached to the nasal chamber perimeter seal 120, this allows the nasal chamber 116 to better seal to the patient's nose.

In a similar manner, a lower lip seal 140 may be provided in the form of a thin elastic membrane spanning the lower portion perimeter seal 120, and has a similar effect of accommodating patients having different size and shape lips, and sealing the nasal chamber even if there was a gap. In various embodiments we provide a nasal bridge seal 100, a lower lip seal 140 or both nasal bridge and lower lip seals 100, 140.

While the invention has particular utility for use with combination the nasal portion of a nasal-oral mask such as described in our aforesaid '934, '277 and '341 PCT applications, the nasal bridge seal 100 and/or lower lip seal 140 advantageously also may be used with conventional nasal masks or full facemasks.

The present invention, in another aspect, provides improvements to the combination nasal-oral mask such as described in our aforesaid '934, '277 and '341 PCT applications, by providing a hinge that allows for relative movement/positioning between the upper nasal chamber and the lower mouth or oral chamber, for better conforming to a patient's face.

Accordingly, in order to accommodate different size/shape faces, we have separated the nasal chamber 200 and the oral chamber 210 into upper and lower portions as shown in FIGS. 4 and 5. The upper and lower portions are connected by an elastomeric hinge 220 or bridge or expansion joint that maintains a seal and yet allows the nasal chamber 200 and the oral chamber 210 to rotate in either direction about the X axis as shown in FIGS. 4 and 5. This rotation allows the perimeter seal to better engage with the nasal bridge and/or the lower lip of the patient. Also, a vertically running elastomeric bridge or hinge or expansion shown in phantom at 222, i.e. connecting the left 224 and right 226 sides of the mask, may be employed in place of or in addition to the elastomeric hinge or bridge connecting the nasal and oral portions of the mask.

While out invention is particularly useful in connection with a combined nasal/oral mask as described in our aforesaid '934, '277 and '341 PCT applications, the invention also advantageously may be employed with conventional masks including full face and nasal masks.

Figure 6:
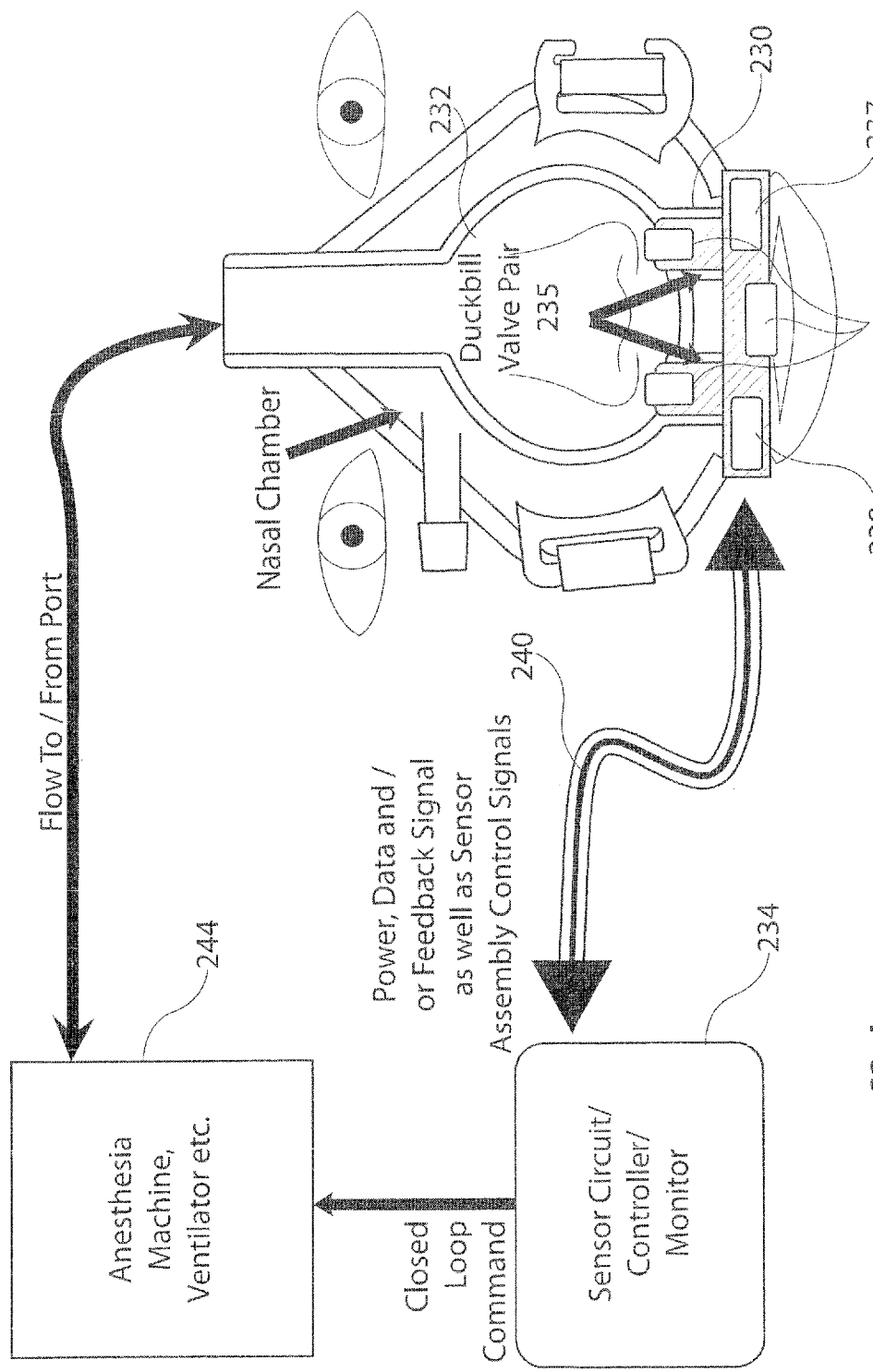
FIG. 6 is a schematic view of a nasal mask and sensor system in accordance with another embodiment of the present invention.

As noted supra, the nasal portion or mask, as above described also provides a platform for supporting various functional attachments and accessories. One such functional accessory is shown in FIG. 6, and comprises an integrated sensor system 230 including one or more sensors 231 carried on proboscises 231 for sensing, e.g., gas identification and concentration levels including, e.g., $O_2$ concentration, $CO_2$ concentration, $N_2$ concentration, anesthesia gas concentration, pressure, relative humidity, temperature and/or gas flow rate, within or adjacent an inner surface and/or outer surface of a ventilation mask 232 and connected to a circuit/controller 234, for monitoring the gas, etc., within or adjacent the mask 232. Preferably the mask comprises a nasal mask with valved ports 235 such as duckbill valves as described in our aforesaid '934, '277 and '341 PCT applications. However, other types of valve mechanisms, or open ports with removable plugs or frangible membranes may be used in place of the duckbill valves. The integrated sensor system within the mask 232 allows sensing of the mask interior environment. Preferably the accessory includes communication capabilities in the form of a circuit/controller 236 and connector 240 that connects to a local amplifier 238 which may include an analog to digital/digital to analog converter. Signals from the sensor system are transmitted to a circuit/controller 234 resulting in a closed or an open loop command that may then be sent to an anesthesia machine, ventilator or other respiratory device 244 to adjust pressure, and various gas properties such as temperature, anesthesia or oxygen concentration and humidity level. The integrated sensor system also may include a local controller 237 for providing local housekeeping, calibration and control functions, etc.

Figure 7:
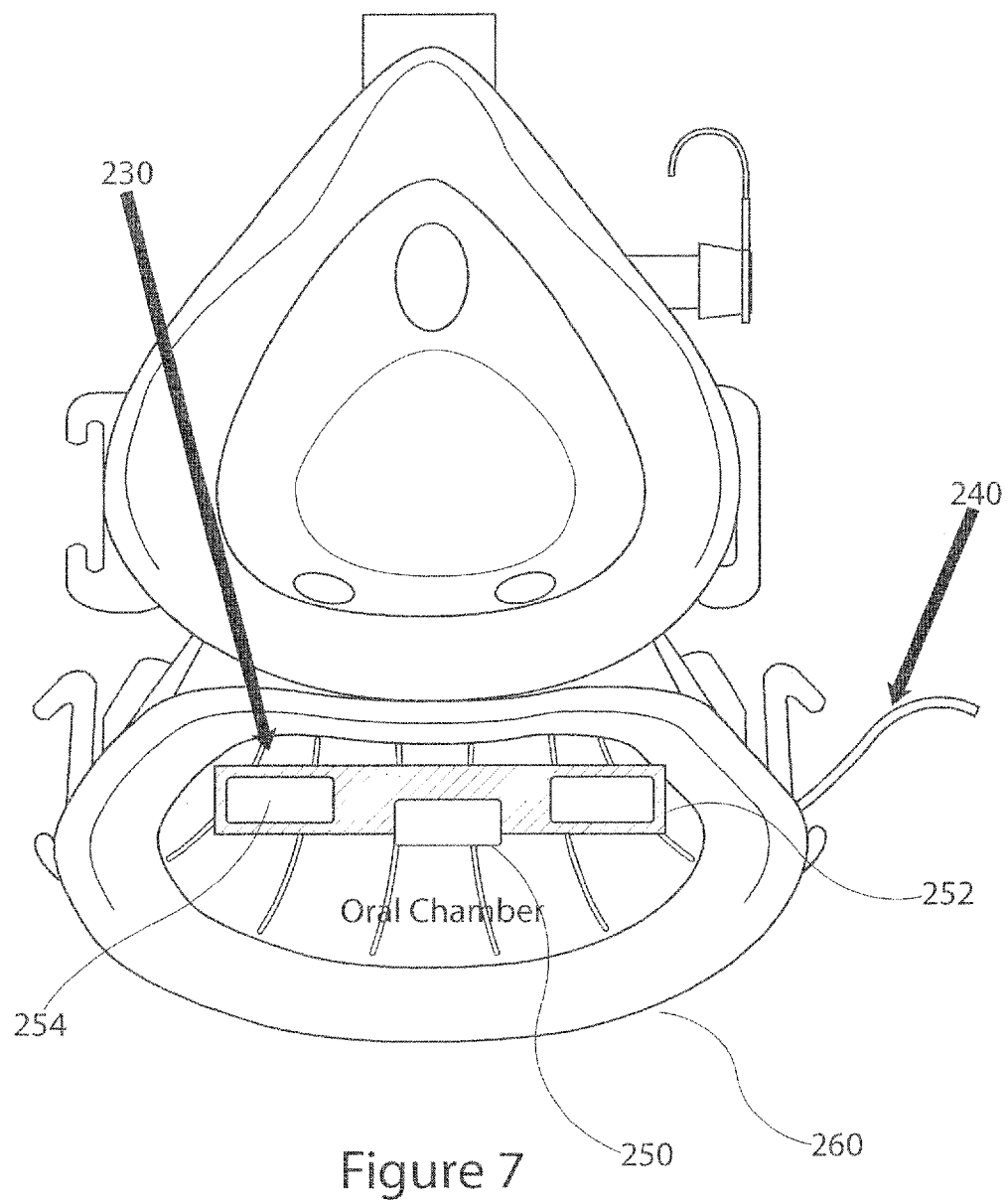
FIG. 7 is an inside view of an embodiment of a combination nasal/oral mask in accordance with the present invention with sensors in the oral chamber.

Referring to FIG. 7 multiple sensors 250, 252 could be placed at different locations within or adjacent the mask inner surface to monitor the inner chamber environment, below the patient's nose where the nasal chamber duckbill valves 260 and the oral chamber 260 proboscis interface, or at other locations. As before, a controller 254 for housekeeping calibration or other functions also could reside in the chamber. All sensor power, data and or control interface may occur through connector 240.

Various other sensors for measuring the above listed and other parameters may be included. The sensors may be (1) resident on an inside of a nasal chamber and/or oral chamber of a combination nasal-oral mask as described above; (2) resident on an inside and also an outside of the nasal chamber; (3) provided as a sensor assembly that plugs into ports of a nasal mask; and/or (4) resident in an oral mask part of a nasal/oral mask combination, without impacting exchange through a connection between the nasal and oral mask portions.

Also provided is a ventilation mask monitor having a local amplifier to amplify sensor signals from one or more of the above sensors, for delivery to a controller, and a ventilation mask monitor including gas sensors, having a power controller for providing filtered power to the sensors and local processor; a ventilation mask gas monitoring system including an Analog to Digital and Digital to Analog signal converter; and a controller for monitoring sensor signals and closing a loop by sending signals to the hardware associated with the airway for one or more of the above parameters.

A feature and advantage of the present invention which results from the placement of a sensor assembly including $CO_2$ or other gas monitors directly within or adjacent an inner surface of a ventilation mask is the ability to monitor the inner chamber environment of the ventilation mask in real time.

Figure 8:
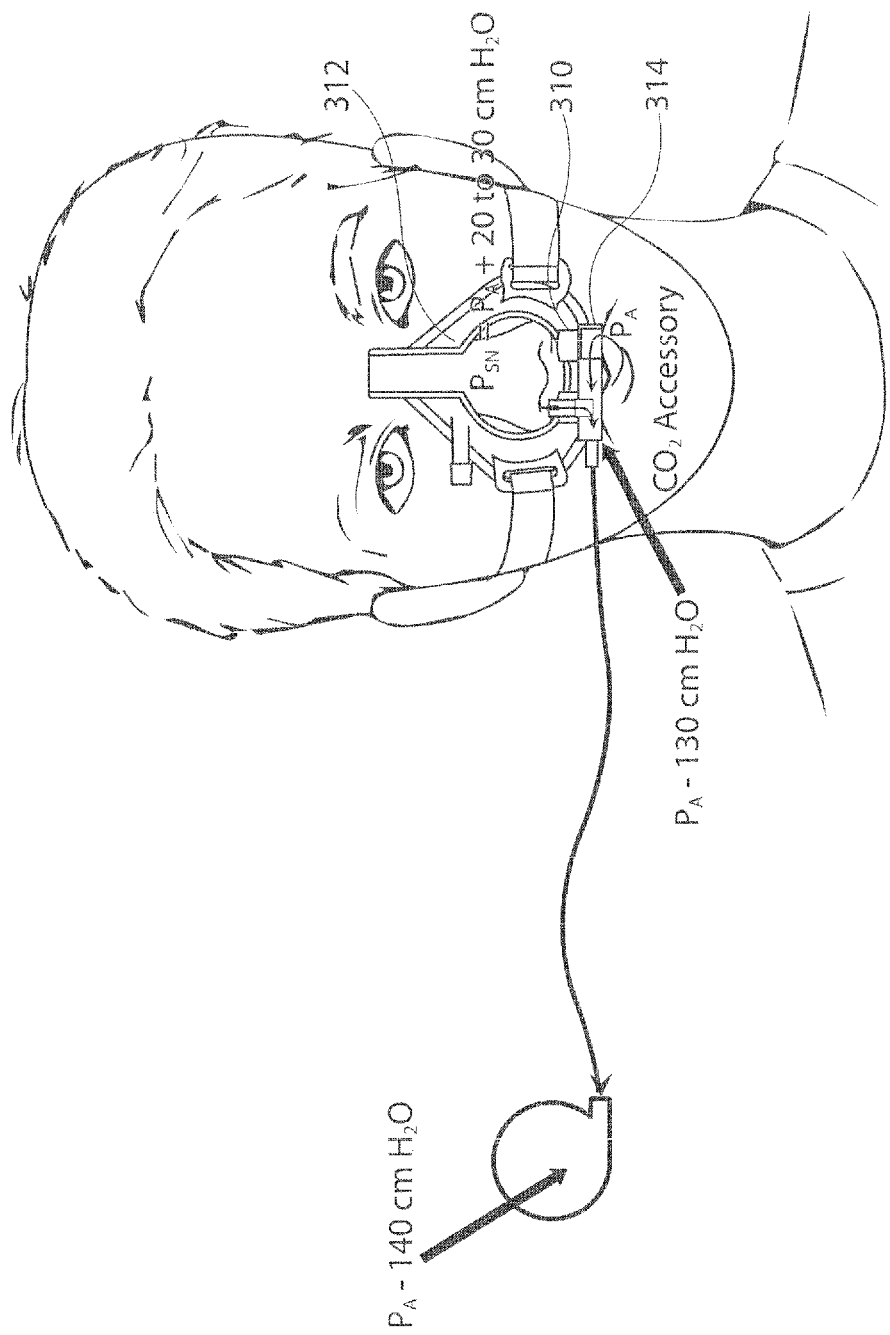
FIG. 8 is a schematic view of a nasal mask with a $CO_2$ collector and gas scavenger accessory in accordance with an embodiment of the present invention.
Figure 9:
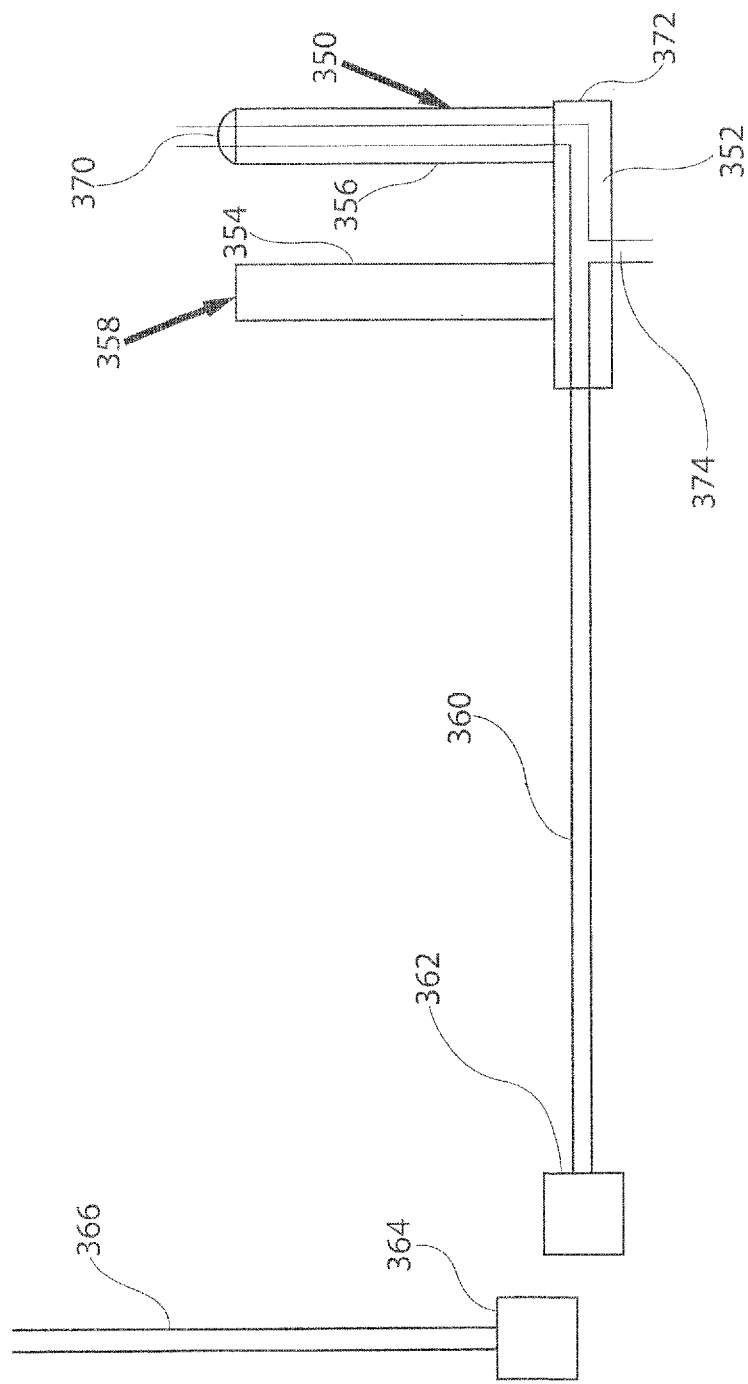
FIG. 9 is a side elevational view of another embodiment of a $CO_2$ scavenger accessory in accordance with the present invention.

Shown in FIG. 8 is a nasal mask which in a preferred embodiment is the nasal portion of a combination nasal-oral mask such as described in our aforesaid '934, '277 and '341 PCT applications, incorporating a sensor assembly 314 which is plugged into the valved ports 310 of the nasal mask 312. Referring also to FIG. 9, the sensor assembly 314 includes a proboscis pair 316 sized and shaped to engage with the valved ports 310 of the mask 312. Sensor assembly 314 includes a plurality of sensor elements 315 for monitoring $CO_2$ and other gas levels such as $O_2$, nitrogen, anesthesia gas concentrations, humidity, etc. Also, if desired, an additional sensor element 315A could be placed exterior to the sensor assembly 314 just above the upper lip of the patient to monitor oral respiratory functions including end tidal $CO_2$.

Sensor assembly 314 engages through the valved ports 310 of the nasal mask 312 to access the nasal chamber interior region and to sit over the patient's upper lip as shown in FIG. 8. When so engaged, the sensor assembly 314 is in direct contact with the interior nasal chamber environment at the top region of the proboscis pair 316. A communication and powerline 320 interfaces with the sensor assembly 314. All sensor elements are interconnected for power, data and control. A description of the sensor elements on the interior to the carrier and proboscis exterior, and partially exterior in the case of sensor element 315A, is provided in Table 1 below:

of the combination mask. The sensor assembly as above described also advantageously may be used in connection with a conventional full face mask.

In yet another aspect of the invention, illustrated in FIG. 9, a functional accessory in the form of an end-tidal $CO_2$ sample line adaptor 350 is provided, which attaches to a nasal mask having valved ports such as duckbill valves as described in our '934, '277 and '341 PCT applications. Sample line adaptor 350 allows end-tidal $CO_2$ monitoring from both the nose and the mouth simultaneously. Preferably sample line adaptor 350 comprises a branched tubing 352, having one or more prongs or proboscises 354, 356 with one or more openings 358. The branched tubing 352 has a line 360 with a luer lock 362 that connects through a standard luer lock 364, which connects to an end-tidal $CO_2$ sample line 366 to monitor end-tidal $CO_2$. The distal end of the branched tubing 352 has two ends with two prongs or proboscises 354, 356, where one prong 356 has a solid proximal end 370 and inserts through the nasal mask's valved ports allowing them to open up, whereby to permit sampling of, e.g., $CO_2$ from the nose. The other end of the branched generally y-shaped tubing 360 has a solid distal end 372 and an open side or slit 374, located on the outside of the nasal mask, near the mouth for sampling $CO_2$ expelled from the patient's mouth.

The current invention is advantageous in that it can monitor end-tidal $CO_2$ from a patient's nose and mouth, while allowing for positive pressure ventilation to occur, and without obstructing either the mouth and/or the view of the patient's airway. This is important because many procedures such as EGD, TEE, and laryngoscopy require the clinician have access to the patient's mouth. Preferably adaptor 350 is thin, and located just above the mouth, so as to not interfere with procedures, or the doctor's view. The inven-

TABLE 1

Nasal Chamber Numbered Elements

| Element # | Name | Comment |
| --- | --- | --- |
| 315/315A | Sensor | One or multiple sensors that monitor the interior nasal chamber environment when mounted at the tip or interior of the proboscis, or the environment above the patient's lip. These sensors can monitor one or more properties, but not limited to:<br>1. Gas Identification and Concentration levels including:<br>    $CO_2$ concentration<br>    $O_2$ Concentration<br>    N Concentration<br>    Anesthesia gas concentrations<br>2. Pressure<br>3. Relative Humidity<br>4. Temperature<br>5. Gas flow Rate |
| 322 | Amplifier/ Converter/ Data Interface | Provides local sensor signal amplification and filtering and/or analog to digital conversion and/or digital to analog conversion and/or digital to digital communication to elements within the Sensor Assembly and external devices. |
| 324 | Local Controller | A local controller could be resident within the assembly to provide for local housekeeping, calibration and control functions |

The sensor assembly provides open and closed loop control of respiratory systems including ventilators, aesthesia machines, CPAP machines, high-flow oxygen and humidification sources.

If a full facemask is desired, composed of a combination mask including both nasal and oral chambers, an alternate configuration is to have a sensor assembly similar to the sensor assembly described integrated into the oral chamber tion also permits positive pressure ventilation without effecting end-tidal $CO_2$ monitoring.

Figure 10:
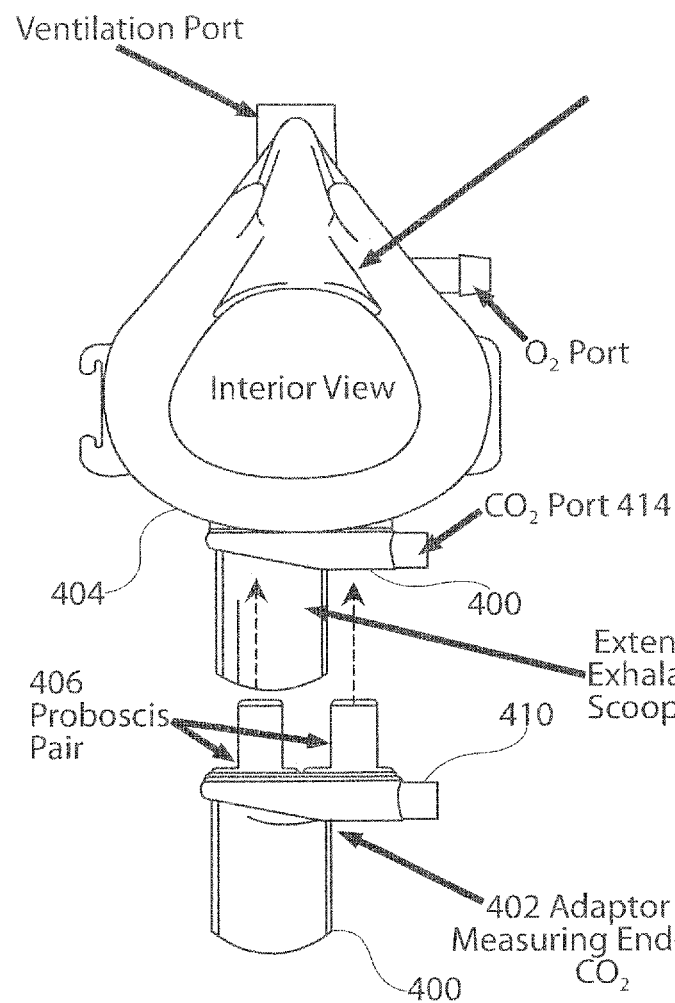
FIG. 10 is a front plan view and FIG. 11 a side view of still another embodiment of the present invention.
Figure 11:
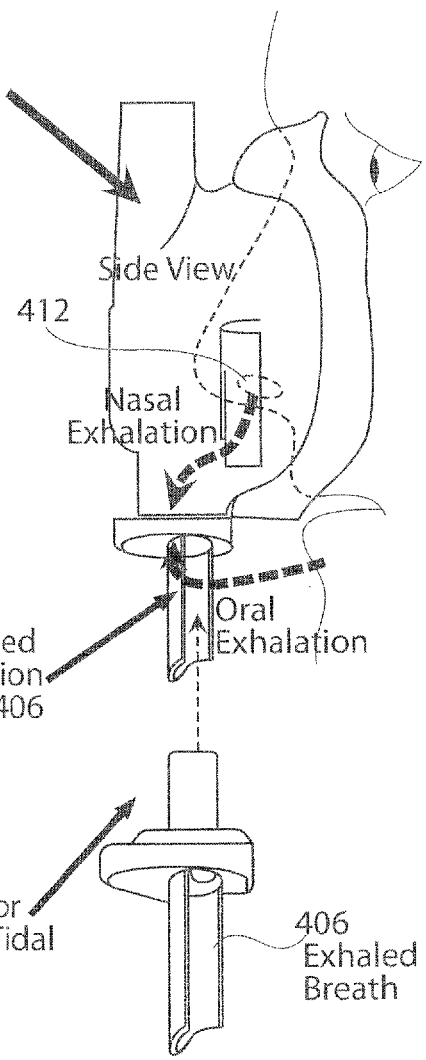

Another embodiment of our invention is shown in FIGS. 10-11. Referring to FIGS. 10-11, in order to better collect end tidal $CO_2$ samples from a patient's exhaled breath, a functional accessory in the form of an exhalation scoop 400 that is part of a nasal chamber adaptor 402 is added to a nasal chamber 404. In one embodiment, the nasal chamber 404 is the chamber portion of a combination nasal-oral mask such as described in our aforesaid '934, '277 and '341 PCT applications. Adaptor 402 has a proboscis pair 406 which engage the valved ports in the nasal chamber 404, which permits collection of nasal exhalation through the proboscis and oral exhalation through the exhalation scoop 400 adjacent the patient's lips. Exhalation scoop 400 directs exhaled breath towards a suction element 410 of a $CO_2$ port when connected to a suction source (not shown). Exhalation scoop 400 preferably is generally perpendicular to the plane created by the patient's lower lip, but may be curved to divert the patient's breath towards the nasal chamber 404.

An extended exhalation scoop 406 that has a length beyond both lips also may be desired in order to capture more of the oral exhalation gases, as shown in the FIG. 11.

Additionally, in order to better scavenge exhaled gas or scavenge exhaled gas and end tidal $CO_2$ from a patient's exhaled breath, an exhalation scoop 412 may be formed as an integral part of the nasal chamber (see FIG. 11).

Exhalation scoop 400, 406 may be rigid, or somewhat flexible to provide access to a user's mouth.

Figure 12:
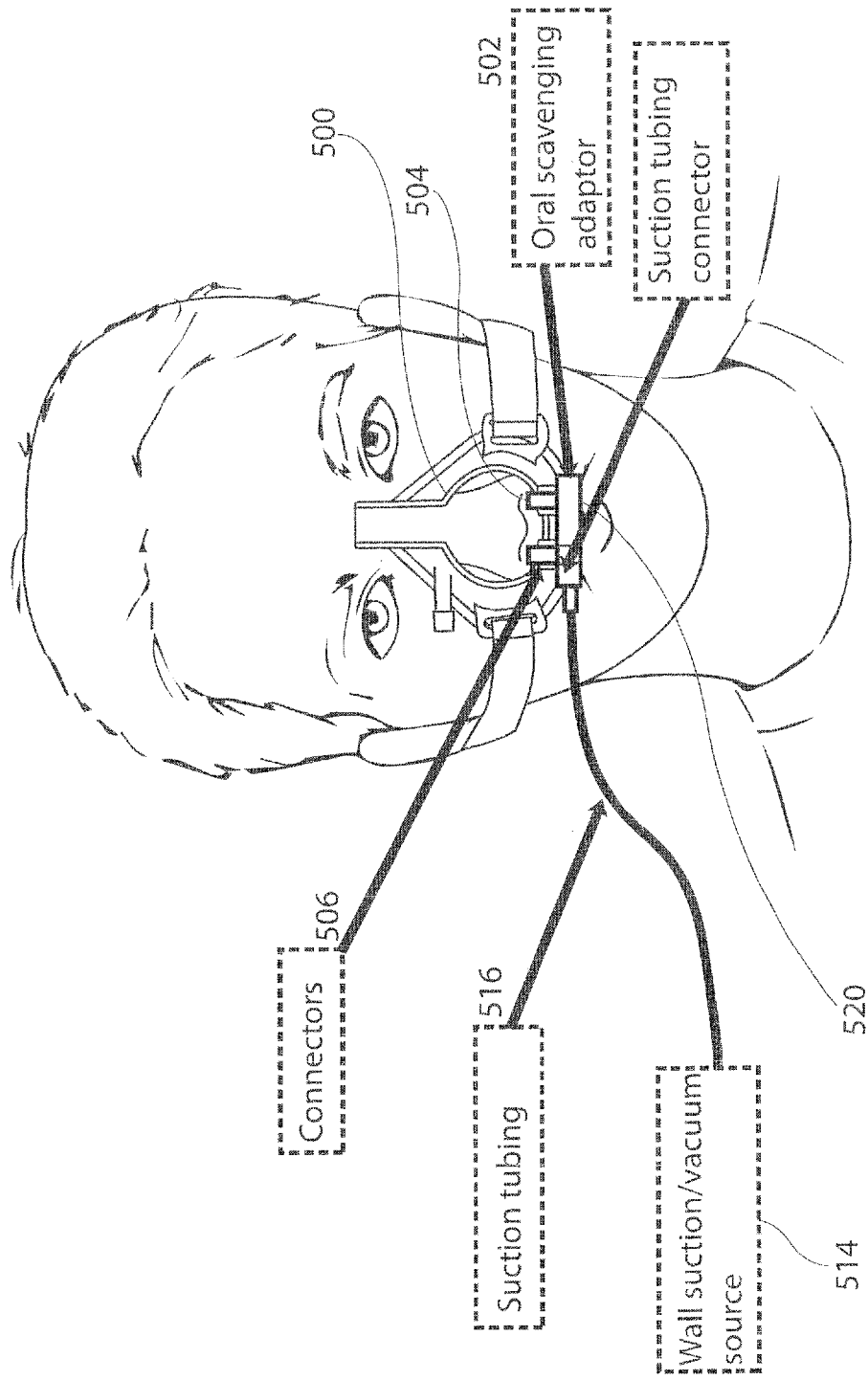
FIG. 12 is a view similar to FIG. 8 of yet another embodiment of the present invention.
Figure 13:
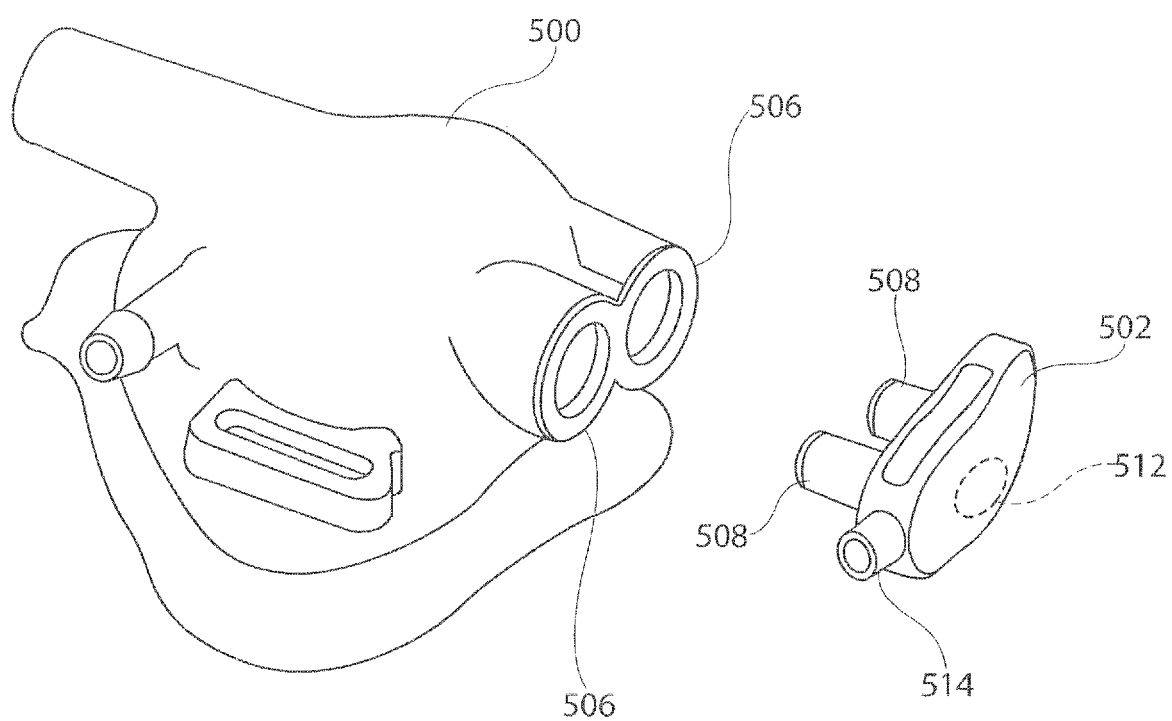
FIG. 13 is an exploded perspective view of yet another embodiment of the present invention.

Referring to FIGS. 12-13 another functional accessory in the form of oral scavenging adaptor 502 is illustrated in which the nasal mask 500 has one or more attachment sites 504, to which an oral scavenging adaptor 502 is connected via ports 506. Preferably the nasal mask comprises a nasal mask portion of the combination nasal/oral combined mask as described in our aforesaid '934, '277 and '341 PCT applications, and the attachment sites 504 are valved ports. However, the oral scavenging adaptor 502 also advantageously may be employed in connection with other, more conventional nasal masks, and may be formed integrally with the mask, or affixed to the mask by adhesive or mechanical fasteners, hook and loop, etc. In a preferred embodiment, the oral scavenging adaptor 502 consists of a hollow member, having an opening 520 on the bottom, and suction tubing 516, connecting the oral scavenging adaptor 502 to a suction or vacuum source 514.

Referring in particular to FIG. 13, in a preferred embodiment, the nasal mask 500 comprises the nasal mask portion of a SuperNO₂VA® mask available from Revolutionary Medical Devices of Tucson, Ariz., and includes ports including a pair of female ports 506 including duckbill valves, and the oral scavenging adaptor 502 comprises one and preferably two closed proboscises 508 sized and shaped to be inserted into the duckbill valves of the nasal mask 500. An opening or port 512 on the lower side oral scavenging adaptor 502 is provided for suctioning anesthetic gases and $CO_2$ which may leak from the patient's mouth. A suction connector 514 connects to suction tubing 516, which in turn connects to wall suction and actively scavenges anesthetic gases.

In a particularly preferred embodiment, the oral scavenging adaptor 502 also includes an end-tidal carbon dioxide monitor (ET-$CO_2$ monitor), for monitoring ET-$CO_2$ from within the nasal mask 500, or the oral scavenging adaptor 502, or both.

As before, while the oral scavenger as above described advantageously may be used with the nasal mask portion of a SuperNO₂VA mask, the oral scavenger adaptor also may be fixed to a conventional nasal mask, using for example, a mechanical fastener, hook and loop fasteners, an adhesive, etc., or the oral scavenger adaptor could be integrally formed as a part of a conventional nasal mask. This allows the clinician to help determine whether or not nasal CPAP that is being applied is effective.

Figure 14A:
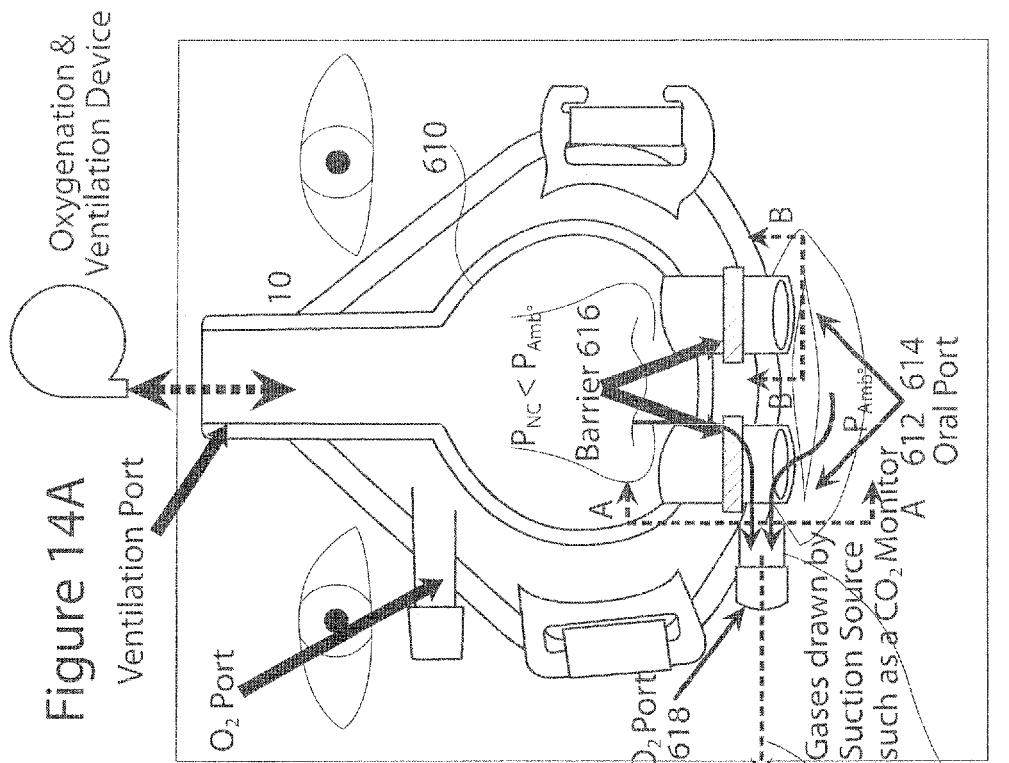
FIG. 14A is a front view.
Figure 14B:
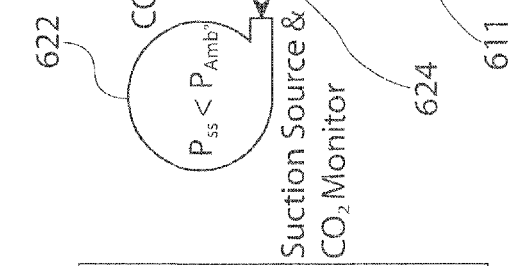
FIGS. 14B and 14C are cross sectional views along sections A-A and B-B, respectively of yet another embodiment of the present invention where an end tidal CO2 collector is integrated as part of the Nasal chamber.
Figure 14C:
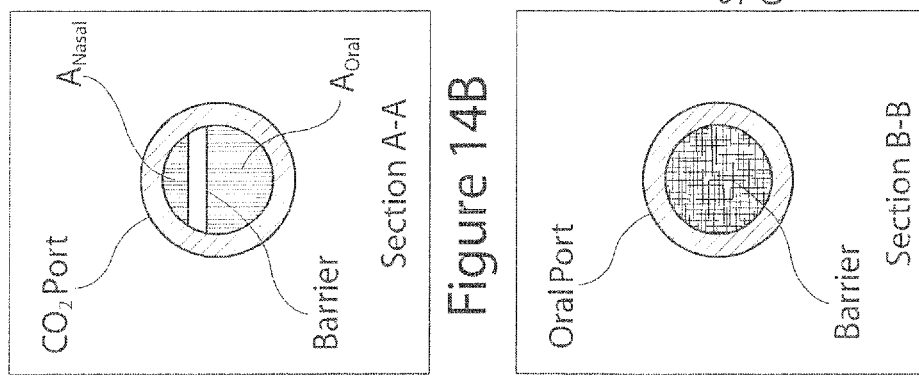

Still yet another embodiment of our invention is illustrated in FIGS. 14A-14C. A nasal mask 610 includes a $CO_2$ port 618 formed as an integral part of the nasal chamber 610 and one or two mounting ports 612, 614. Ports 612, 614 have barriers 616, that separate the pressure environment within the nasal chamber 610, $P_{NC}$, from the ambient pressure environment where the patient's lips are located, $P_{Amb}$. This provides a seal so that the nasal chamber interior may be pressurized at a level that is greater than ambient. $CO_2$ port 618 intersects the port 612 at barrier 616. The intersection of the $CO_2$ port 618 at barrier 616 can be adjusted such that the area that provides an opening to the interior of the nasal chamber environment, $A_{Nasal}$, and the area providing an opening to the ambient environment of the oral region, $A_{Oral}$, can be sized to adjust the level of flow from zero flow to full flow based on suction source negative pressure, $P_{ss}$ from the nose and mouth accordingly ($P_{ss}<P_{Amb.}<P_{NC}$). A flow would occur when the end of the $CO_2$ port 618 is attached to a suction and sampling device such as a $CO_2$ monitor 622. The open end of the $CO_2$ port 618 is connected to the suction source by a tube or pipe 624.

This configuration allows the nasal chamber to be maintained at adequate positive pressure while still allowing sampling end tidal $CO_2$ that is being expired from the nose and the between the lips. Additionally, this configuration provides the benefit that if anesthetic gasses are being expelled from the mouth, some or all of those gasses will be scavenged through the oral port when connected to a suction source such as a $CO_2$ monitor 622.

An alternate configuration shown in FIGS. 15A and 15B adds as a functional accessory an integrated gas scavenger or collector 626 that attaches to a suction source 628 that is used to scavenge anesthetic gases. A configuration with only the gas scavenger 626 also is possible. The gas scavenger 626 consists of a scavenger port 630 that intersects the oral port 632 as shown in Section B-B of FIG. 15A. In this configuration, only the ambient oral environment called out as $A_{Oral}$, will be exposed to the suction source, resulting in the collection of expired gases from the mouth by the suction source. The nasal chamber is blocked from the suction source. The open end of the scavenger port 630 is connected to the suction source 628 by a tube or pipe.

Incorporating a $CO_2$ collector as part of a nasal mask has several advantages. For one, the $CO_2$ collector or scavenger port does not obstruct access to or visualization of the oral cavity of the patient. Also, the $CO_2$ collector has a secondary benefit that it may be used to scavenge anesthetic gases expired from the mouth.

Alternatively, a $CO_2$ collector such as an exhalation scoop may be formed as an integral part of the nasal mask, to sample end tidal $CO_2$ from a patient's exhaled breath. FIGS. 16A and 16B illustrate front and side views, respectively, of an exemplary exhalation scoop 640. The exhalation scoop 640 includes one and preferably two closed proboscises 642 sized and shaped to be inserted into the duckbill valves of the mask. Preferably proboscises 642 are formed of a relatively rigid material for engaging with the duckbill valves, while the main body 644 of the exhalation scoop is formed of a relatively soft compliant material so as to not injure or irritate the patient if it is pushed against the patient's lips or teeth. Exhalation scoop extends from a forward, lower surface of the oral ports of the mask and directs the exhaled breath of the patient towards the suction element of the $CO_2$ port 650. Exhalation scoop 640 should be a gas impervious barrier that directs flow of the exhaled gas from the patient's mouth toward the collection suction provided by the $CO_2$ port when connected to a suction source. In an alternative embodiment one or both proboscises 642 are hollow so that breath collected by the exhalation scoop 640 may be diverted into the nasal mask and a port on the nasal mask for connection to a suction source. The exhalation scoop 640 may be located nominally perpendicular to the plane created by the lower lip of the patient, but preferably is curved to divert the breath towards the nasal chamber.

Figure 16D:
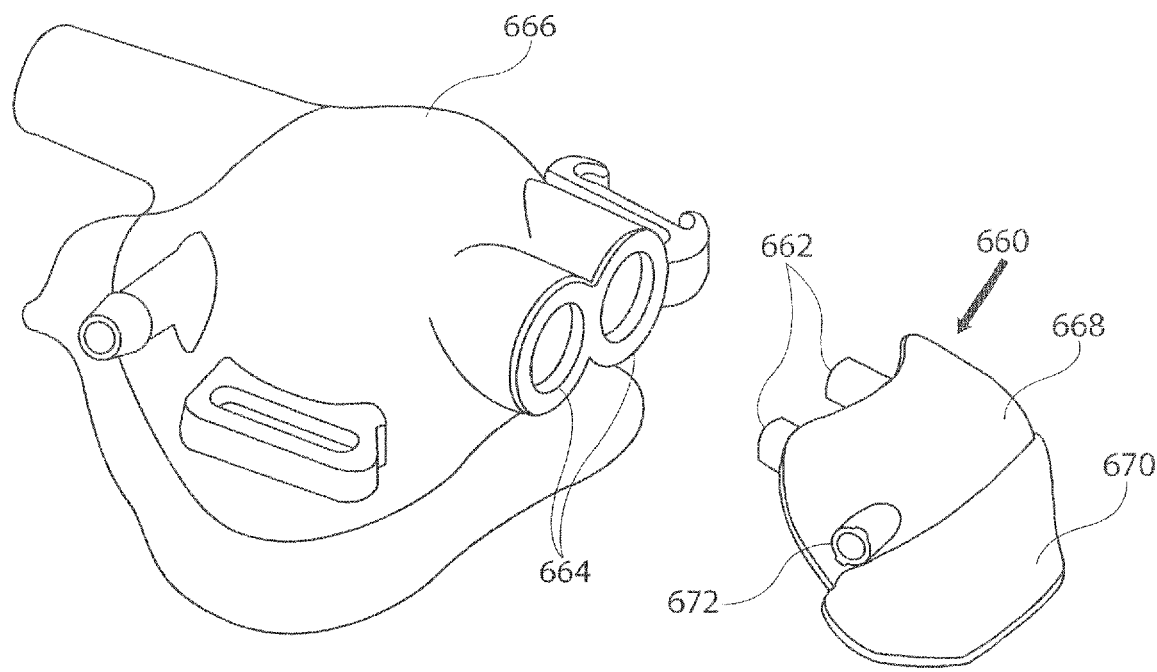
FIG. 16A is a front view, FIGS. 16B and 16C side views, FIG. 16D an exploded view and FIG. 16E a rear view of yet another embodiment of the present invention where an end tidal CO2 collector and gas scavenger are integrated as part of the nasal chamber (FIGS. 16A and 16B), or formed separately and mounted to the nasal chamber (FIGS. 16C-16E)
Figure 16C:
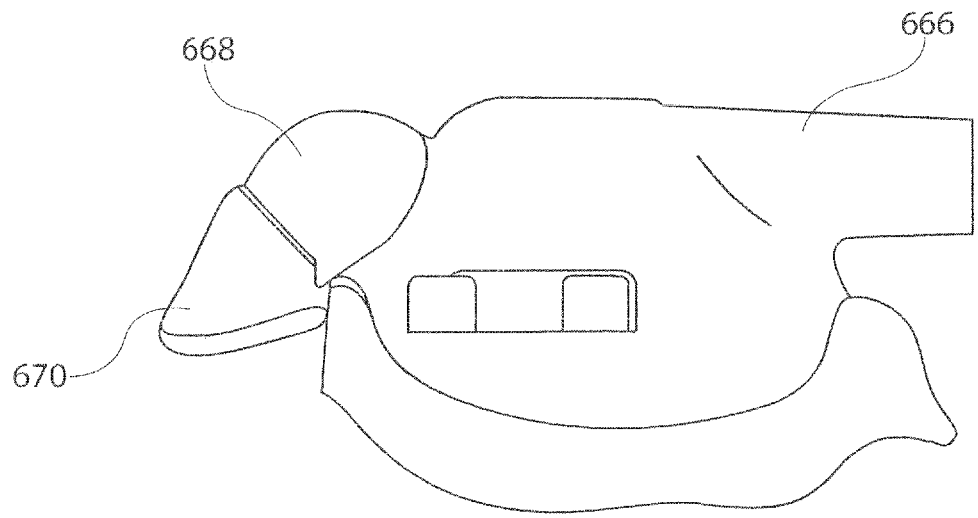
Figure 16E:
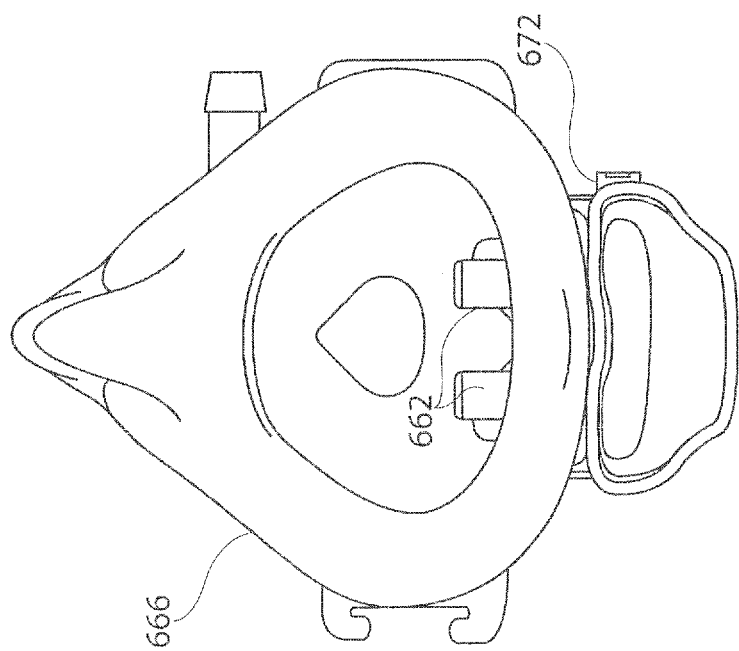

Alternatively, as shown in FIGS. 16C-16E, an exhalation scoop 660 may be formed separately with closed proboscises 662 sized and shaped to be inserted into the duckbill valves 664 of the nasal mask 666. Preferably the proboscises 662 and main body 668 of the inhalation scoop 660 are formed of a relatively rigid material, while the distal portion of the exhalation scoop 660 is formed of a relatively soft compliant material so as to not injure or irritate the patient if it is pushed against the patient's lips or teeth. Exhalation scoop 660 includes a CO2 port 672 which may be connected to a suction source. In an alternative embodiment, one or both proboscises 662 are hollow so that breath collected by the exhalation scoop 660 may be diverted into the nasal mask and a port on the nasal mask for collection to a suction source.

Figure 17:
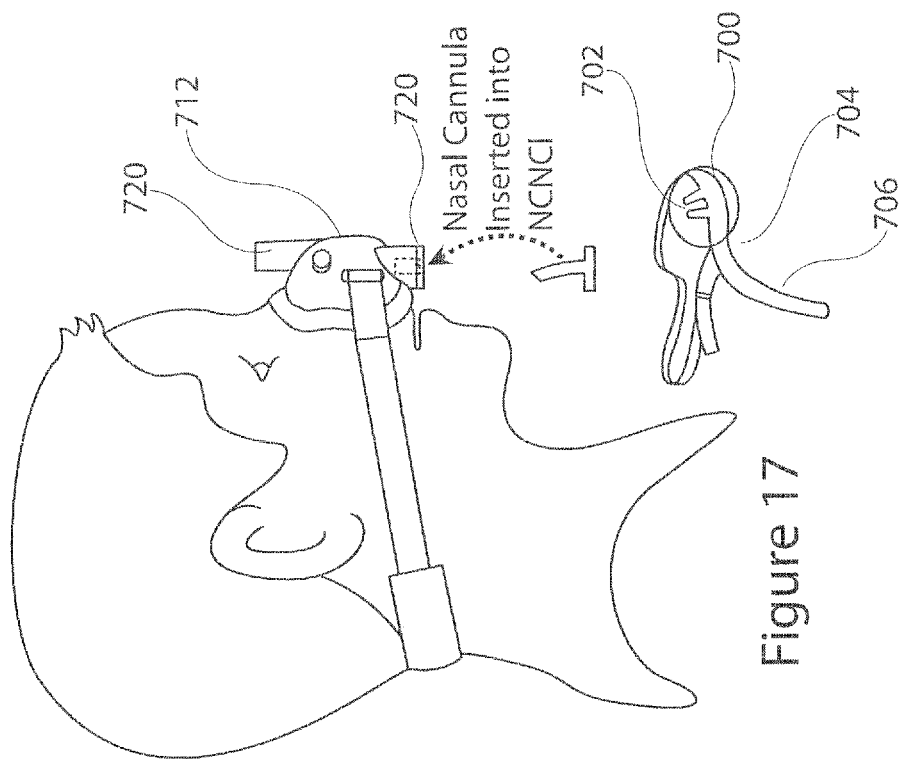
FIG. 17 is an exploded side elevational view of still yet another embodiment of the present invention where a nasal cannula accessory is inserted through the duckbill valves to provide additional oxygen flow.

In yet another aspect, the present invention provides a functional accessory in the form of an adapter for converting or supplementing a nasal mask to/with a high flow nasal cannular system. In one embodiment of the invention, illustrated in FIG. 17, there is provided a high flow nasal cannula attachment piece 700 (nasal chamber to nasal cannula interface), which consists of a male end 702 and a female end 704, where the female end 704 connects to a conventional high flow nasal cannula systems 706 (such as an OptiFlow™ nasal cannula available from Fisher & Paykel Healthcare, or a VapoTherm™ nasal cannula available from Vapotherm, Inc.), and the other end 702 attaches to the ports 720 on a nasal mask. Unlike conventional high flow cannulas which are relatively soft so as to not damage a patient's tender nares, the male end 702 of the high flow nasal cannula 700 attachment is made sufficiently rigid or stiff distally to allow for penetration through the duck valves in the ports 720 of the mask nasal chamber 712 to maintain patency of the valves. The male end 702 of the nasal cannula should be made long enough to reach the nares of the patient. Attachment piece 700 can either be used as an open system by connecting to a nasal mask with a seal and leaving a circuit port open, or be used as a closed system, connecting to nasal mask with a seal, with its circuit connector connected to either a ventilator, resuscitation bag, CPAP machine or PEEP valve, in order create a positive pressure inside the mask or full facemask, and allow for positive pressure ventilation.

Positive pressure also allows for relief of upper airway obstruction and allows for institution of mask ventilation. With this configuration, gas flows can be achieved that surpass the capabilities of current high flow nasal cannula systems and are over 100 L/min. e.g. through the mask inlet port 720.

Figure 18:
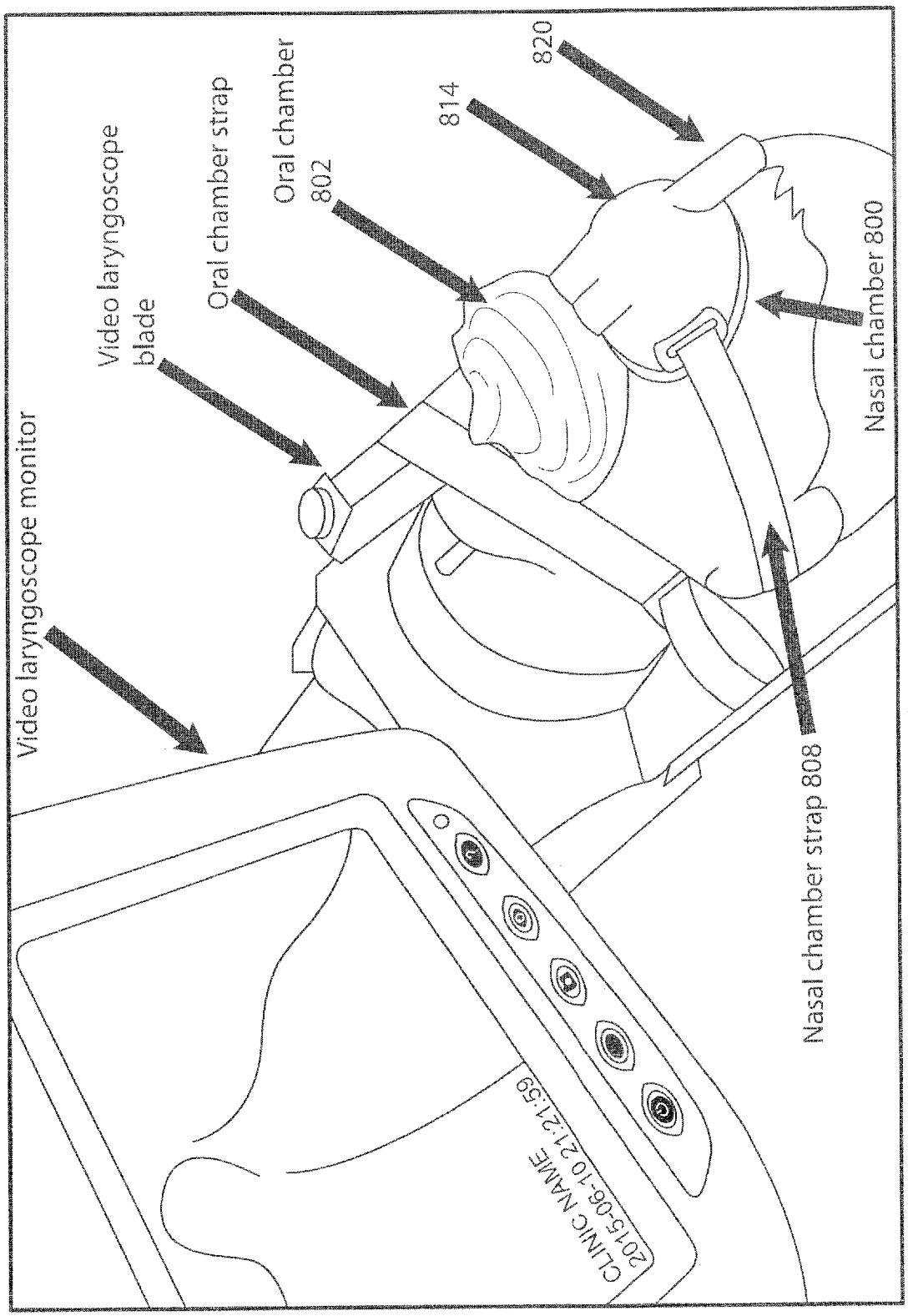
FIG. 18 is perspective view of another embodiment of the invention in which a video laryngoscope blade is inserted through the oral chamber.
Figure 19:
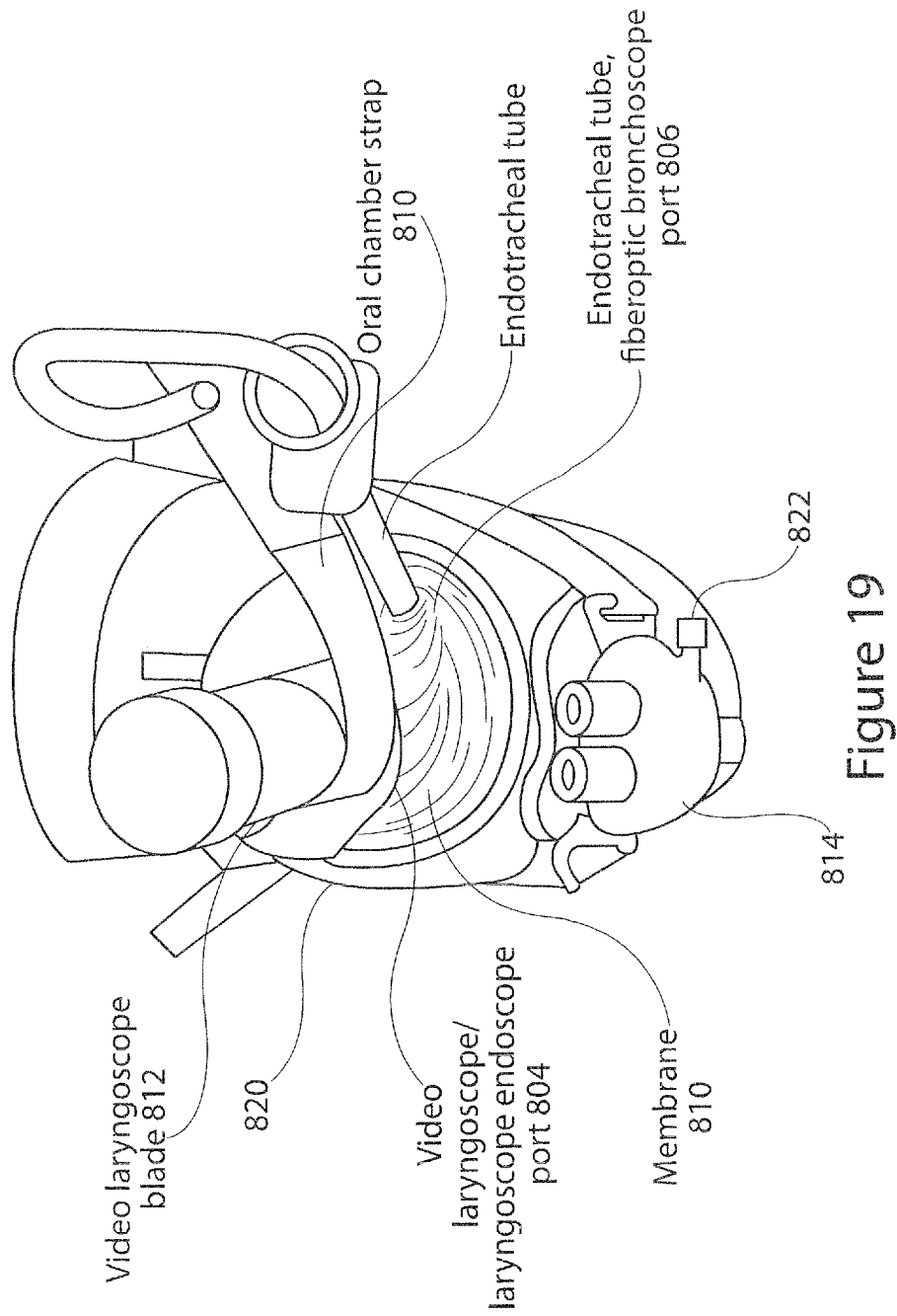
FIG. 19 is a perspective view of another embodiment of the invention in which a video laryngoscope blade and an endotracheal tube are inserted through the oral chamber.

Still other embodiments of the invention are illustrated in FIG. 18-19 which illustrate the present invention with a functional adaptor for art endotracheal tube or video laryngoscope. Endotracheal intubation is considered a dangerous procedure, since it is performed without the patient receiving any oxygen or being ventilated. The amount of time it takes to place an endotracheal is critical, as too long may cause the patient's oxygen saturation levels to fall to life-threatening levels. Also, many times it may take several attempts to place an endotracheal tube, at which point a patient's oxygen saturation level may fall to life-threatening levels (desaturation). Patients that are in respiratory failure who need to be emergently intubated or patients that are morbidly obese whose oxygen stores are quickly used up, may only have a few seconds after they have received their last breath until their oxygen saturation levels fall to life-threatening levels and their heart goes into deadly arrhythmias.

The present invention provides a gas ventilation mask comprising an anesthesia nasal mask 800 and a mouth mask 802 defining respectively a nasal chamber and an oral chamber, where the nasal chamber is connected to a gas supply (mechanical ventilator, anesthesia machine, oxygen supply source) and used to provide oxygenation and ventilation and the oral chamber is used to create a seal around the patient's mouth to prevent leakage of gas, and accommodate a laryngoscope or other instrument as described below.

The nasal mask portion may be a conventional nasal mask or specialty nasal mask such as described in the aforesaid '934, '277 and '341 PCT Applications.

The oral mask portion has one or more ports 804, 806 which contain either one-way valves such as duck bill valves (not shown) similar to the duck bill valves described above for the nasal masks, capped ports, or membranes 810 which allow the passage of, e.g., a video laryngoscope, and handle, endotracheal tube, and/or fiberoptic bronchoscope, with an endotracheal tube attached 812 and seals the video laryngoscope/laryngoscope, endotracheal tube, and/or fiberoptic bronchoscope with an endotracheal tube 812 to prevent any leakage of gas around them.

In use, the nasal mask 814 is placed over the patient's nose and secured to the patient's head by a strap 808, which creates a seal around the nose and prevents leakage of gas. One nasal mask port 820 is connected to a gas supply where the gas supply is pressurized and can be used to deliver oxygen and ventilate the patient. In another embodiment a second port 822 can be used to connect to a gas supply.

As noted supra, the oral mask may have one or more ports 804, 806, wherein each port is either a one-way valve or a membrane that allows for the passage of, e.g., a video laryngoscope blade 812 and/or handle and either an endotracheal tube and/or a fiberoptic bronchoscope with an endotracheal tube attached through one or more ports and also creates a seal around the video laryngoscope/laryngoscope blade and/or handle as well as the endotracheal tube and/or the fiberoptic bronchoscope with the endotracheal tube attached. The oral mask also covers and seals the mouth, and is held in place by an oral chamber strap 810 preventing any leakage of gas.

In one embodiment the oral mask has two ports, where one port 804 allows for a video laryngoscope to pass through and seal around it, while the second port 806 allows for either an endotracheal tube and/or fiberoptic bronchoscope with an endotracheal tube attached to pass through and seal around it to prevent any leakage of gas. In yet another embodiment a third port 820, may be provided, for connection to a gas supply and allow the oral mask to be pressurized and allow for oxygenation and positive pressure ventilation.

In one embodiment, the oral chamber is adapted to attach and seal to the video laryngoscope/laryngoscope. In a further embodiment the oral chamber could be carried on the video laryngoscope/laryngoscope.

In yet another embodiment, the oral chamber may be provided with one or two extensions, which can be inserted into one or both of the patient's nares and seal the nares, whereby to prevent leakage of gases and eliminate the necessity for a sealed nasal chamber as described above and illustrated in FIG. 17. In another embodiment, a closed and pressurized system with one or more ports allows for the delivery of oxygen positive pressure ventilation, and monitoring of end-tidal carbon dioxide as described above. Also, if desired, end-tidal carbon dioxide can be sampled and monitored from one or more ports within either the oral chamber, the nasal chamber, or both chambers, also as described above. Also, for patients who are spontaneously breathing (i.e., breathing on their own), the nasal chamber can be used to apply continuous positive airway pressure (CPAP) to keep the patient's airway patent, while the oral chamber prevents any gas from leaking out of the mouth and maintains the pressure within the patient's airway.

In a further embodiment, where the oral chamber occludes the patient's nares and is connected to the pressurized gas supply, when the patient is spontaneously breathing, CPAP can be used to keep the patients airway patent (open).

In another aspect the oral mask includes a port through which the endotracheal tube may pass, which can act as a guide when passing the endotracheal tube into the trachea to facilitate endotracheal intubation. In another embodiment, the oral chamber has one or more ports which allow for the passage of an gastroenterology endoscope and rigid bronchoscope while maintaining a seal around them.

In yet another aspect there is provided a multi-port gas ventilation mask system that allows for the passage of a video laryngoscopy/laryngoscope, endotracheal tube, fiberoptic bronchoscope, rigid bronchoscope, gastroenterology endoscope, and suctioning tubing with an endotracheal tube, and which includes a nasal mask and a mouth mask defining respectively a nasal chamber and an oral chamber, where in the desired embodiment the mask seals touch adjacent the top of the mouth, so that the nasal mask and the mouth mask may be used separately with the nasal mask providing oxygenation and ventilation, and the oral mask maintaining a seal to provide a closed system. Also provided is a mask anchor for holding a face mask on a patient, which includes a head support for engaging a back of a patient's head, a posterior head strap that originates from behind the patient's head, in contact with the patient's head and attaches either directly or indirectly to the mask when the mask is on the patient's face, wherein the strap can be tightened to create a seal to allow for positive pressure ventilation or left loose and for providing supplement oxygen. Also provided is an anesthesia mask strap system having a first expandable strap portion having the ability to extend; second and third non-expandable strap sections fixed to ends of the first expandable strap section; and an adhesion section for fixing a length of the strap system when the second and third non-expandable strap sections are pulled to tension the expandable strap section.

Also, while the oral ventilation mask has been shown as having a flexible membrane with ports for accommodating and sealing around a laryngoscope and endotracheal tube, the membrane may be formed of a flexible self-sealing material which the clinician may puncture to introduce a laryngoscope or endotracheal tube, and self-seal around the laryngoscope or endotracheal tube.

Other changes are possible. For example, a full face mask or an oral only mask may be provided with a sealing membrane for permitting introduction of a laryngoscope, or other instrument.

The present invention in yet another aspect provides improvements in respiratory nasal and/or full face mask and breathing circuit assemblies. Over the last decade the number of moderate and deep sedation procedures have dramatically increased (several million being performed annually). Sedation cases use sedating medications in order to limit the patient from experiencing both physical and psychological pain. However, these sedating medications can cause relaxation of the muscles that help maintain an open airway (i.e., upper airway obstruction), which can lead to the airway becoming obstructed, inhibiting the patient from breathing. Also, if a higher than expected dose of sedating medication is given it can lead to respiratory depression.

Current practice recommends using a supplemental oxygen mask and a carbon dioxide ($CO_2$) monitor in order to try to maintain a patient's blood oxygen levels at or close to oxygen saturation. However, even with these devices, a patient may still suffer life-threatening complications such as oxygen desaturation (low blood oxygen levels).

Typically, a clinician would either apply a continuous positive airway pressure (CPAP) mask over the patient's nose and mouth to relieve a possible upper airway obstruction, or a ventilation mask is placed over the patient's mouth and nose and the patient is bag-mask ventilated using one of several non-rebreathing breathing circuits (Mapleson, Bain, Magill and Lack, Jackson Rees, etc). However, many procedures such as endoscopy, transesophageal echocardiography (TEE), and bronchoscopy require that the surgeon have access to the patient's mouth, which prevents clinicians from being able to use this life-saving technique. Thus, one of the major drawbacks to current non-rebreathing breathing circuits is the fact that they are used with a full ventilation facemask, which covers the patient's nose and mouth.

The present invention provides an improvement over the foregoing non-rebreathing breathing circuits and other prior art breathing circuits and helps to solve the problem of patient's desaturating and becoming apneic during moderate and deep sedation procedures, by providing either nasal CPAP to relieve an upper airway obstruction, or nasal NIPPV via a pressurized breathing circuit connected to supplemental oxygen to nasally or nasally/orally bag-mask ventilate.

More particularly, the present invention provides improved breathing circuits, which includes but is not limited to non-rebreathing breathing circuits, controllable partial rebreathing anesthesia circuits, and a non-rebreathing anesthesia circuits. Provided is a non-breathing breathing circuit comprising a fresh gas supply line either directly connected to an exhalation collecting tube or completely separate from the exhalation collecting tube where one end of the exhalation collecting tube is connected to either a nasal ventilation mask, a two chamber (nasal chamber with removable oral chamber) full ventilation facemask, or a nasal ventilation mask with an oral seal/scavenger, and the other end is connected to a flexible reservoir having bag walls. One end of the fresh gas line can either be directly connected to the exhalation collecting tube or it can be separately connected to the nasal mask or full facemask, while the other end is connected to the fresh gas supply. The bag defines a passageway for flow of gas in a first direction. The bag has a gas outlet and inlet, where the outlet is in communication with an exhalation collecting tube, which defines a passageway for flow of gas in a second direction. At least part of the walls of the bag extend beyond the sides of the collecting tube, and the first and second directions of gas flow are substantially parallel to, and laterally offset from, one another. Alternatively, the exhalation collecting tube is attached to an outer surface of the reservoir bag. The present invention allows either a reusable or disposable non-rebreathing breathing circuit to be connected to either a nasal mask, a full facemask, or a nasal/oral mask configuration, which can be used to create a seal to maintain positive pressure while simultaneously allow the passage of a tool such as a video laryngoscopy/laryngoscope, an endotracheal tube, a fiberoptic bronchoscope, a rigid bronchoscope, gastroenterology endoscope, or suction tubing.

Thus, the present invention in another aspect provides a breathing system, which can be used to deliver gases to a patient via either the nose or both the nose and mouth using blow-by flow, continuous positive airway pressure (CPAP), or non-invasive positive pressure ventilation (NIPPV), and to remove gases exhaled by the patient including $CO_2$ and anesthetic gases via a exhalation collection tube. The circuit may be used with an oxygen tank for transportation of the patient from one location to another, or connected to supplemental wall oxygen used in an operating room, or in a procedural room such as a GI suite, cardiac catheter lab, MRI, or bronchoscopy suite. A flexible reservoir bag defines a passageway for flow of gas in a first direction, the bag having a gas outlet and inlet, wherein the bag outlet is in communication with the exhalation collecting tube which defines a passageway for flow of gas in a first and a second direction. In one embodiment of the invention, at least part of the walls of the bag extend beyond sides of the exhalation collecting tube, and the gas flow first and second directions are substantially parallel to, and laterally offset from, one another.

The invention also provides a non-rebreathing breathing circuit for delivering oxygen through a mask to a patient, which may be either reusable or disposable, for connection to either a nasal mask, a full face mask, or a nasal mask and oral mask set in which the oral mask and nasal mask are separate from one another, wherein the full face mask or the oral mask includes a valved connector or membrane seal for maintaining positive pressure while simultaneously allowing passage of a tool such as a video laryngoscopy/laryngoscope, an endotracheal tube, fiberoptic bronchoscope, a rigid bronchoscope, gastroenterology endoscope, and/or suction tubing to scavenge gases.

The present invention also provides a non-rebreathing breathing circuit for delivering oxygen through a mask to a patient, that can be used to deliver gases to a patient via either the patient's nose or the patient's nose and mouth using blow-by flow, continuous positive airway pressure (CPAP), or non-invasive positive pressure ventilation (NIPPV), and to remove gases exhaled by the patient via an oral scavenger or pressure release valve.

The above-described non-rebreathing breathing circuits may be used in combination with a portable oxygen tank for transportation of the patient from one location to another, or connected to supplemental wall oxygen used in an operating room, or used in procedural room such as a suite, cardiac catheter lab, MRI, and bronchoscopy suite. In such embodiment a fresh gas line and an exhalation collecting tube preferably are connected to a nasal chamber portion of a full face two chamber combined nasal and oral facemask, wherein the oral chamber is removable allowing the nasal chamber to stay on the patient and to be used for nasal CPAP and nasal NIPPV, while simultaneously allowing the surgeon access to the patient's mouth to perform the procedure.

The present invention also provides a non-rebreathing breathing circuit system for delivering oxygen through a mask to a patient, where a fresh gas line and an exhalation collection tube line is connected to a nasal mask for use in nasal CPAP and nasal NIPPV, said system further including a separate oral mask, wherein the oral mask has a valved connector or membrane seal that allows passage of a tool such as a video laryngoscope/laryngoscope, endotracheal tube, and/or fiberoptic bronchoscope with an endotracheal tube attached and/or suction tubing.

In still yet another embodiment of the invention there is provided a non-rebreathing breathing circuit for delivering oxygen through a mask to a patient, wherein a fresh gas line and an exhalation collection tube are directly connected to either a nasal mask, a full facemask having a valved connector or membrane seal that allows passage of a tool such as a tool such as a video laryngoscope/laryngoscope, endotracheal tube, fiberoptic bronchoscope with an endotracheal tube and/or a suction tube, a nasal mask/oral mask combination in which the oral mask is separable from the nasal mask, or an oral mask and oral mask set in which the oral mask and nasal mask are separate from one another, wherein the oral mask has a valved connector or membrane seal that allows passage of a tool such as a video laryngoscope/ laryngoscope, endotracheal tube, fiberoptic bronchoscope with an endotracheal tube.

In various of the above embodiments the mask may include a port for scavenging gases, an/or an exhalation collecting tube including an end-tidal $CO_2$ port for connection to an end-tidal $CO_2$ monitor, and/or filters for absorbing $CO_2$.

Figure 20:
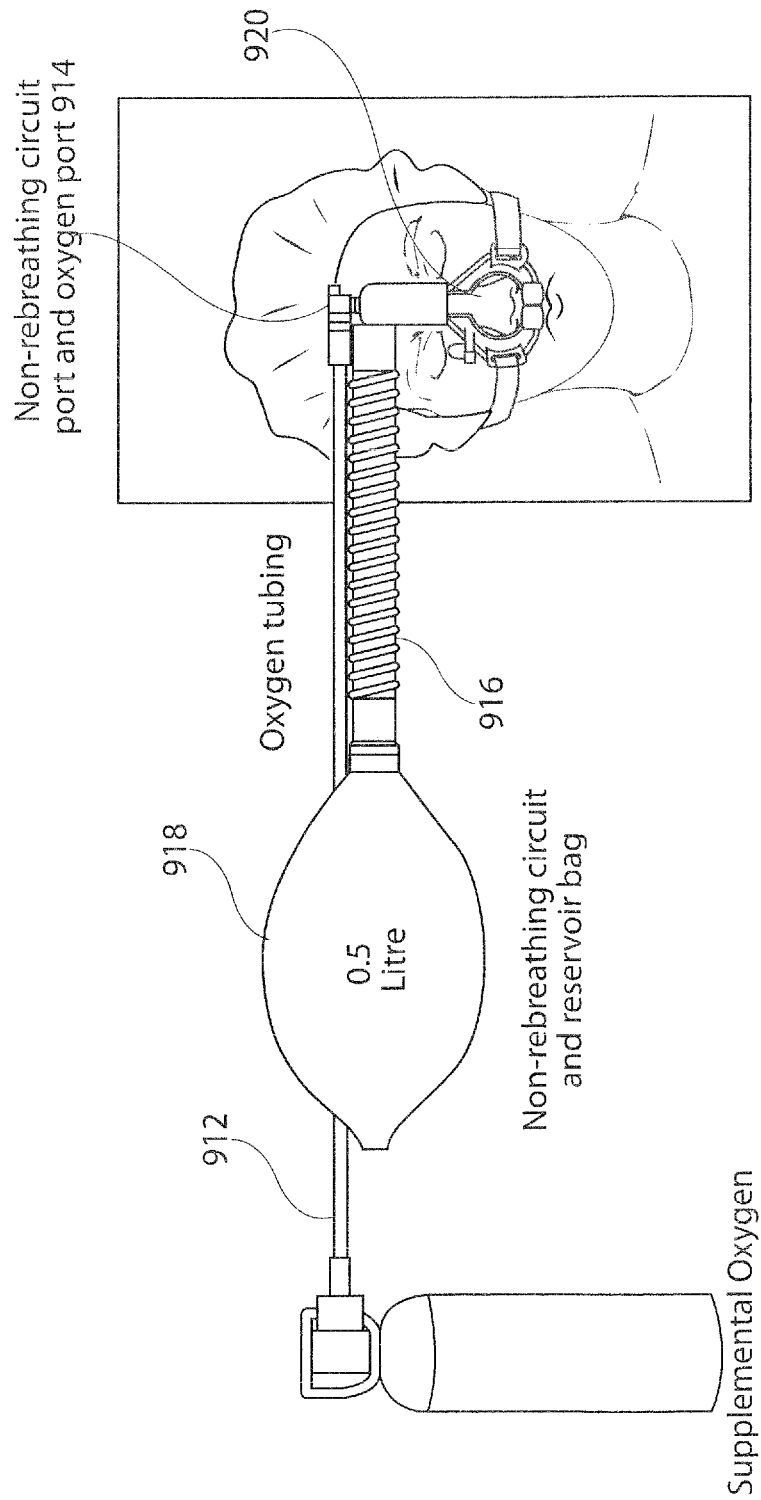
FIG. 20 is a schematic view showing yet another embodiment of the invention including a respiratory nasal mask and breathing circuit assembly.

Referring to FIG. 20 there is shown a non-rebreathing breathing circuit, wherein a fresh gas line 912 is connected to an exhalation port 914 of a nasal ventilation mask 920. An exhalation collection tube 916 is also connected at one end to the exhalation port 914, and at its other end to a reservoir bag 918. As so constructed, the non-rebreathing breathing circuit permits nasal CPAP and nasal NIPPV while simultaneously allowing a surgeon access to the patient's mouth 922 to perform a procedure, i.e. allow passage of a tool such as a video laryngoscope/laryngoscope, an endotracheal tube, a fiberoptic bronchoscope, a rigid bronchoscope, a gastroenterology endoscope, or suction tubing, etc.

Figure 21:
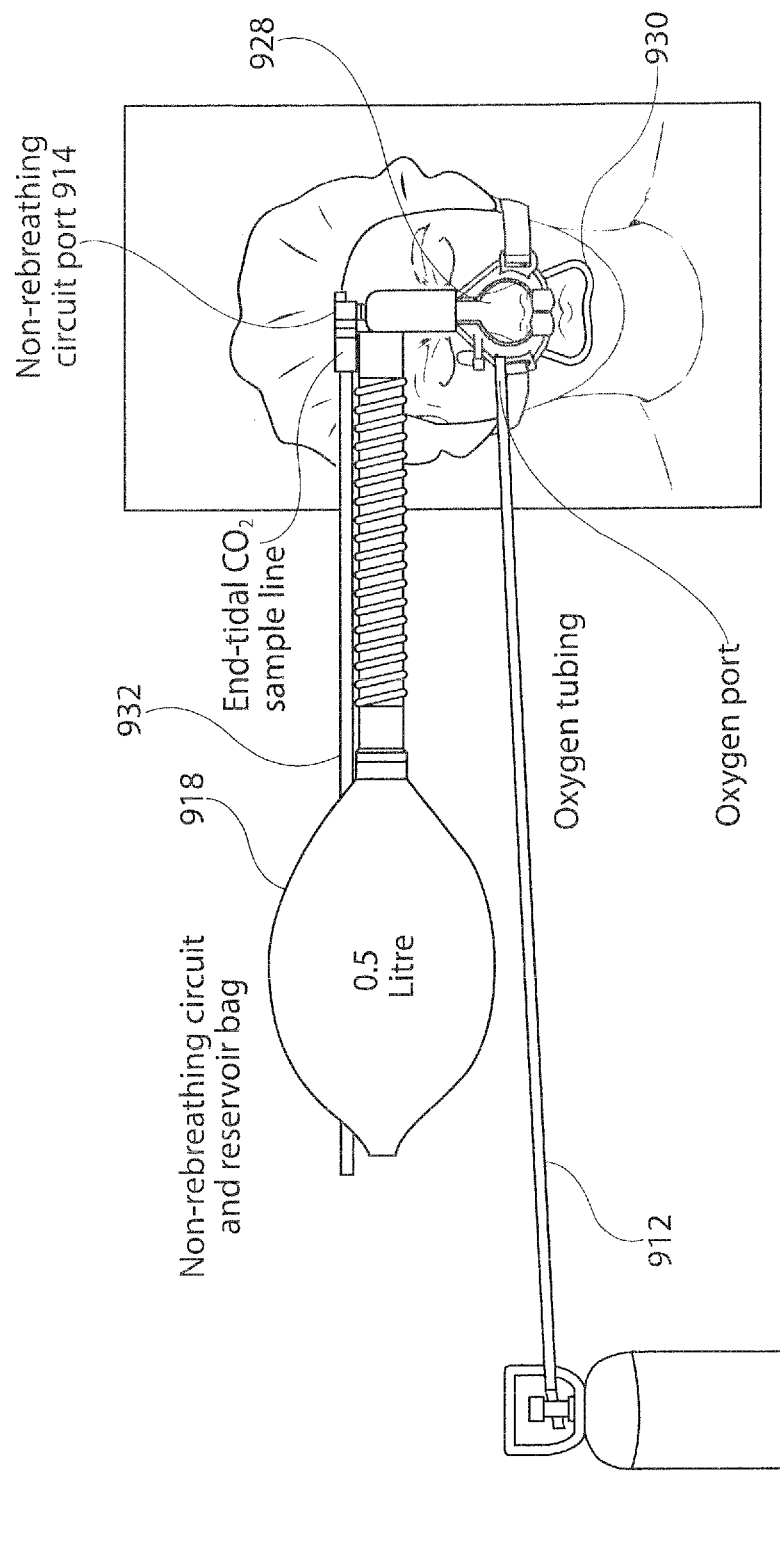
FIG. 21 is a schematic view of yet another embodiment of the invention comprising of a respiratory tube chamber (oral and nasal) full face mask and breathing circuit assembly.

In another embodiment of the invention, shown in FIG. 21, a fresh gas line 912 is connected to the exhalation port 914 of the nasal mask 928, which nasal mask in turn is connected to a removable oral ventilation mask 930 in accordance with our aforesaid '934, '277 and '341 PCT Applications. With such arrangement, the oral ventilation mask 930 may be removed, allowing the nasal mask 928 to remain on the patient and used for nasal CPAP and nasal NIPPV while simultaneously allowing the surgeon access to the patient's mouth to perform a desired procedure, e.g. endoscopy, etc. Also, with this embodiment, an end-tidal $CO_2$ sampling line 932 is connected to the exhalation port 914 of the nasal mask 928.

Figure 22:
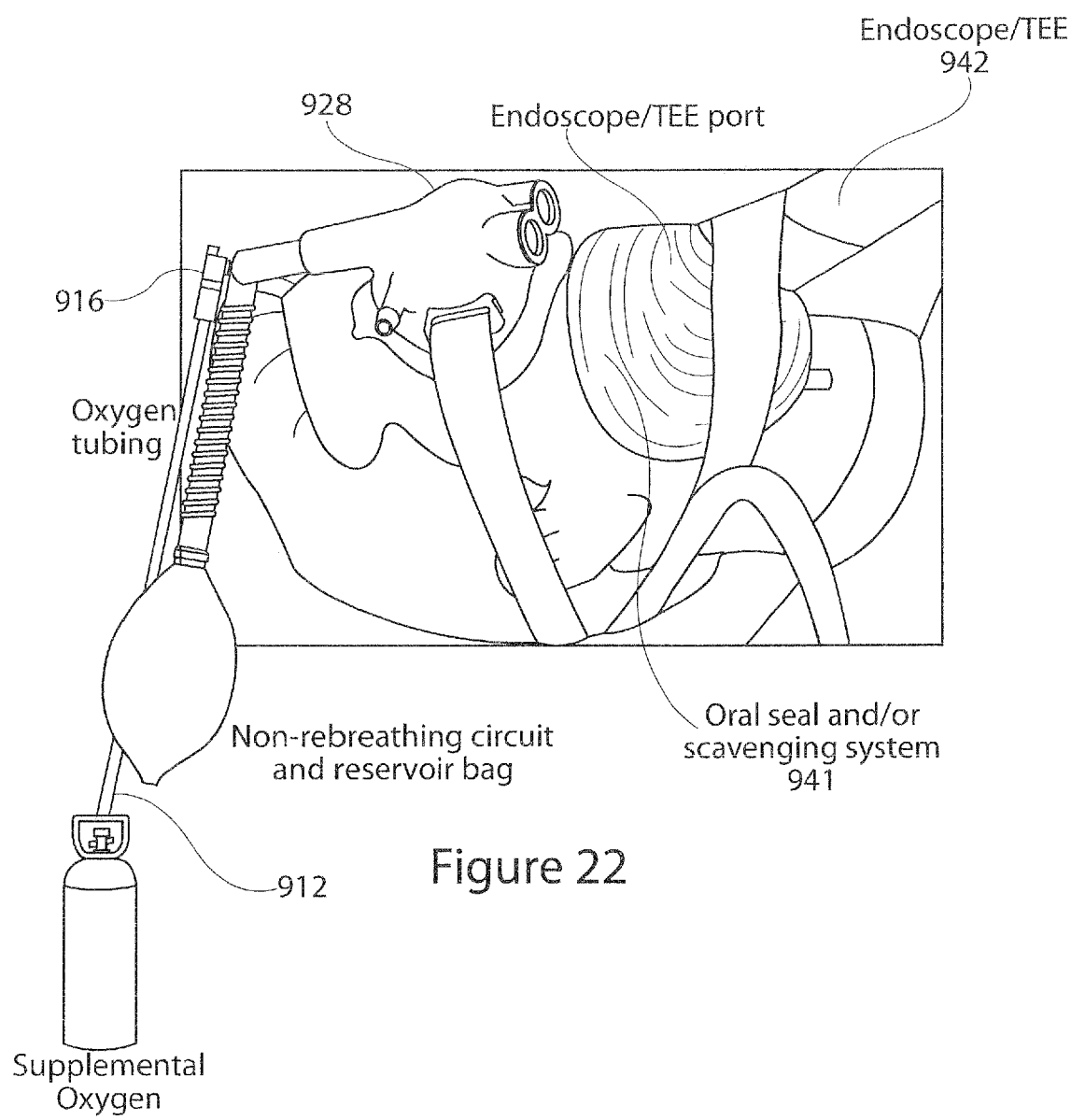
FIG. 22 is a schematic view of yet another embodiment of the invention incorporating separate nasal and oral masks with a breathing circuit assembly through the oral mask.

Yet another embodiment of the present invention illustrated in FIG. 22 comprises a separate nasal mask 928 and oral mask 940. The fresh gas line 912 is connected to the exhalation port 916 to the nasal mask 920, as in the case of FIG. 20. In the illustrated exhibit, the oral mask 940 comprises one or more ports 942 which contain either one-way valved connector or membrane seal to accommodate the passage of a endoscope or other tool such as a video laryngoscope/laryngoscope, endotracheal tube, fiberoptic bronchoscope, or suction tubing, etc. while at the same time sealing the tool to prevent leakage of gas around the tool. The oral mask 720 also can be used to scavenge exhalation gases.

Figure 23:
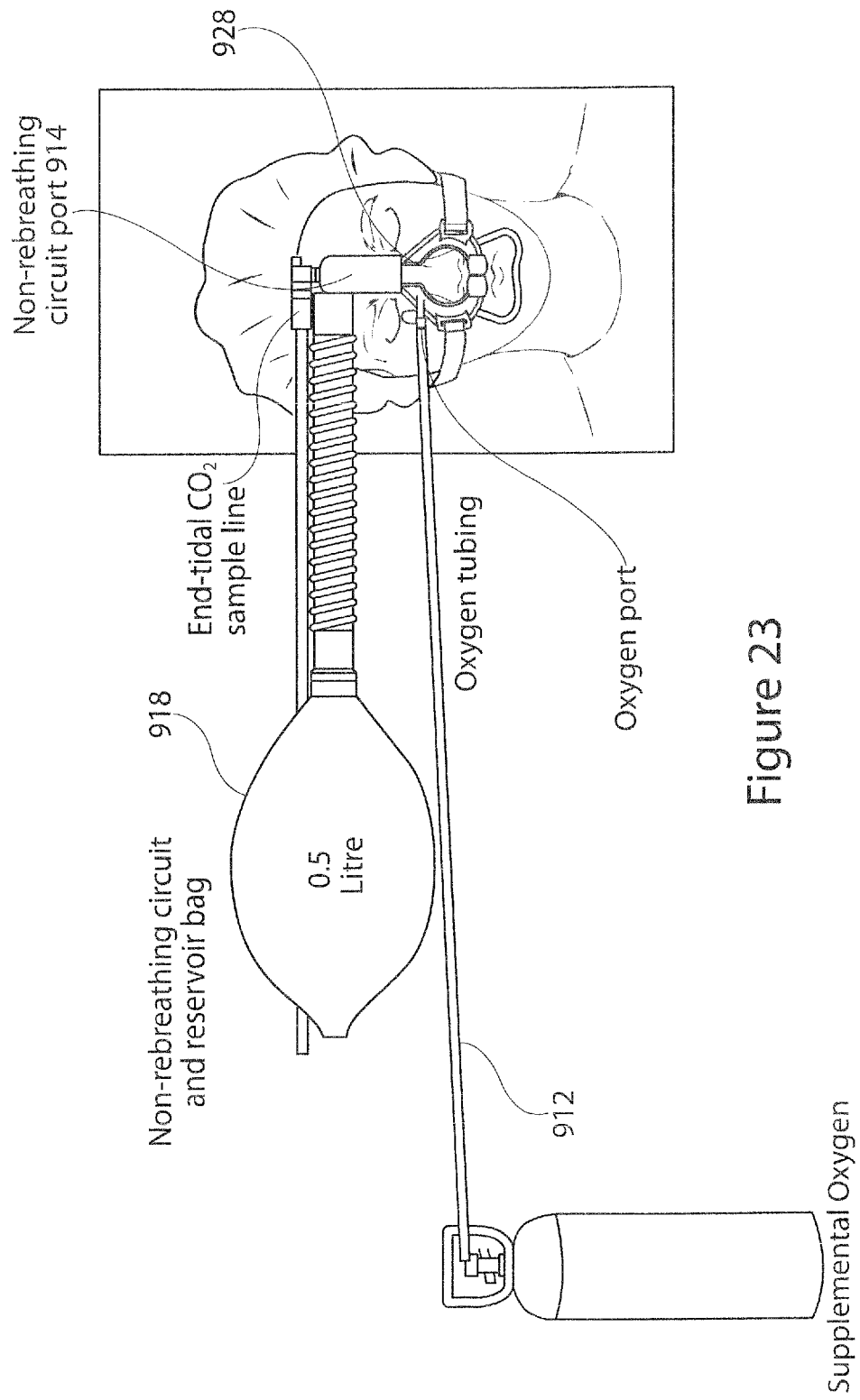
FIG. 23 is a schematic view of yet another embodiment of the invention showing a respiratory nasal mask directly connected with a fresh gas limb and breathing circuit assembly.
Figure 24:
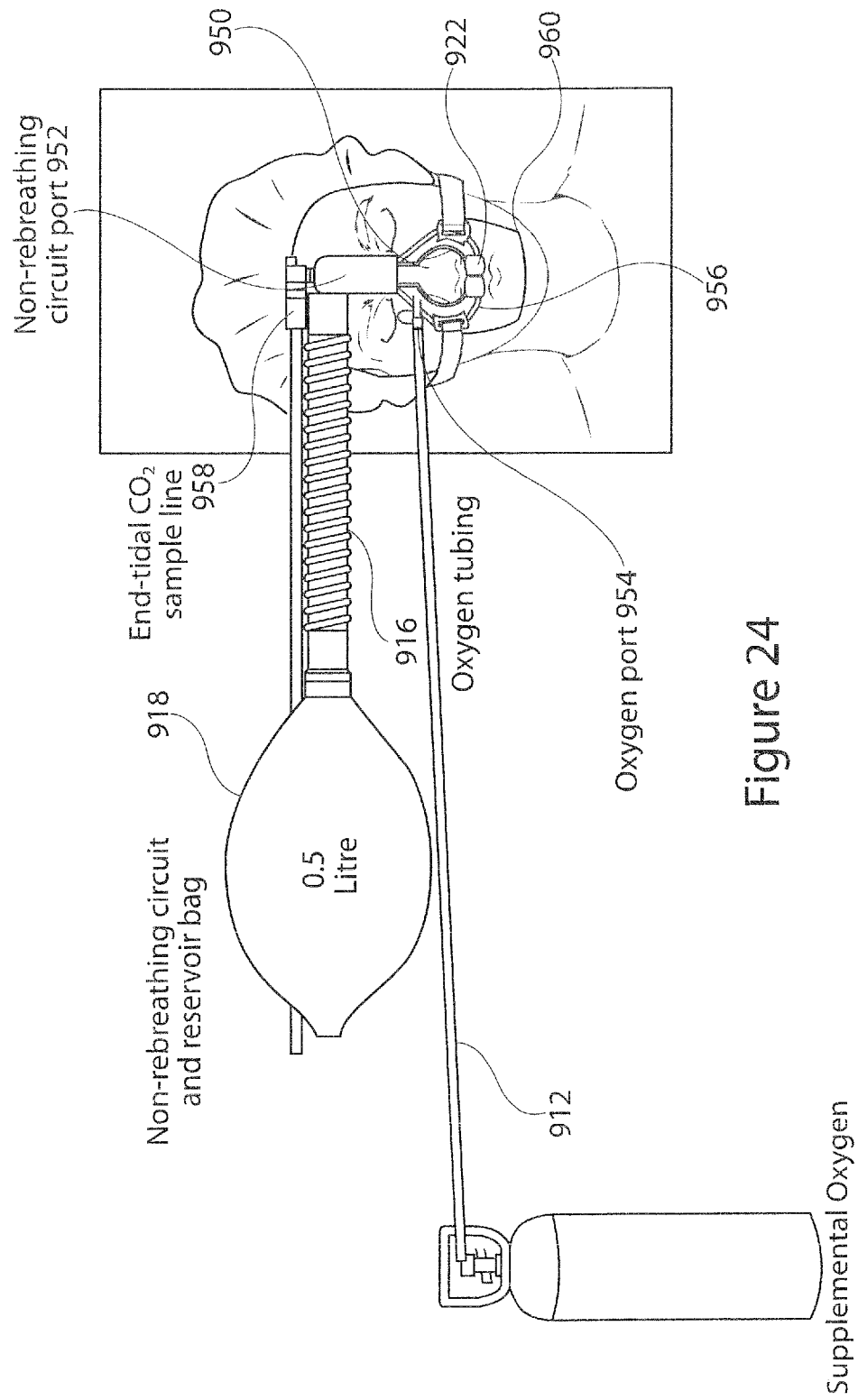
FIG. 24 is a schematic view of another embodiment of the invention showing a two-piece full face mask and breathing circuit assembly.

Yet another embodiment of the present invention, shown in FIG. 23 is similar to the nasal mask portion of the nasal mask/or mask combination shown in FIG. 21. Still yet another embodiment of the invention is illustrated in FIG. 24. In the FIG. 24 embodiment the mask comprises an two-piece face mask including a nasal mask 950 and an oral mask 960, which includes a non-breathing circuit port 952 and oxygen port 954, and includes one or mounting ports 956 which support an oral ventilation mask 960 similar to oral ventilation mask 930 shown in FIG. 21. Alternatively, oral ventilation mask 960 may be similar to oral ventilation mask 802 shown in FIG. 18, and include membrane seals to allow the passage of a tool such as a video laryngoscope/laryngoscope, endotracheal tube, fiberoptic bronchoscope with an endotracheal tube, suction tool, etc to seal the tool to prevent leakage of gas around them.

If desired, a separate end-tidal $CO_2$ sampling line 958 and/or gas scavengers may be provided, connected to the non-rebreathing circuit port collection tube 916.

A feature and advantage of the present invention is that the fresh gas line 912 is completely separate from the exhalation line. This allows for end-tidal $CO_2$ monitoring through a port 952, and also allows for an easier manufacturing, since the fresh gas line will not have to be incorporated into the exhalation collection tube.

Also, while the invention has been described in connection with non-re-breathing breathing circuits, the invention also advantageously may be used with controllable partial rebreathing circuits, and non-rebreathing anesthesia circuits. The present invention allows either a reusable or disposable non-rebreathing breathing circuit to be connected to either a nasal mask, a full facemask, or a nasal/oral mask configuration, which can be used to create a seal to maintain positive pressure while simultaneously allow the passage of a tool such as a video laryngoscopy/laryngoscope, an endotracheal tube, a fiberoptic bronchoscope, a rigid bronchoscope, gastroenterology endoscope, or suction tubing.

In other embodiments the mask may be used with pressure regulated or low flow CPAP; a full face mask can connect to a nasal mask without losing pressure as an (1) attachment, (2) built into a mask, or (3) with a ventilator or anesthesia machine.

Still yet other embodiments are possible. For example, a bacteria or $CO_2$ filter may be build into the mask connector. Also, a pop-off valve with pressure relief may be provided at the $O_2$ port. Also, if desired, nebulized or aerosolized medication may be injected via the $O_2$ port. Also, the $O_2$ port may be provided with a 1-way valve for a person delivering breaths.

The present invention is the only full face mask that can convert to a nasal mask for CPAP that can connect to supplemental $O_2$ tank, and the only positive pressure ventilation mask providing high flow $O_2$ capability utilizing $O_2$ post and ventilation post simultaneously with minimal leakage.

Finally, the present invention is a new configuration for a disposable continuous positive airway pressure (CPAP) system. Disposable continuous positive airway pressure (CPAP) systems function by applying a continuous flow of gas (i.e.: oxygen) to a closed and regulated system (i.e., a mask), which allows pressure to be built up within the mask. This pressure is then transmitted to a patient's airway and can be used to apply a continuous positive airway pressure. This is typically used for patients that have either Obstructive Sleep Apnea or an upper airway obstruction from sedation.

The present invention is unique in that it can convert from a nasal CPAP mask to full facemask CPAP mask and vise versa while continuously maintaining pressure within the mask the entire time. The configuration is also unique in that the nasal mask's supplemental oxygen port can also be used as an exhaust port to prevent the re-breathing of carbon dioxide.

In a preferred embodiment the nasal CPAP mask comprises a nasal mask having a circuit port and an exhaust port, one or more attachment ports and an adaptor for connecting a PEEP valve and supplemental oxygen to the mask.

In another and preferred embodiment the one or more attachment ports include closures such as duck bill valves for engagement by proboscises of an oral chamber when attached to the nasal chamber.

The present invention also provides a disposable CPAP system comprising a nasal mask as above described, and a removable oral mask.

Figure 25:
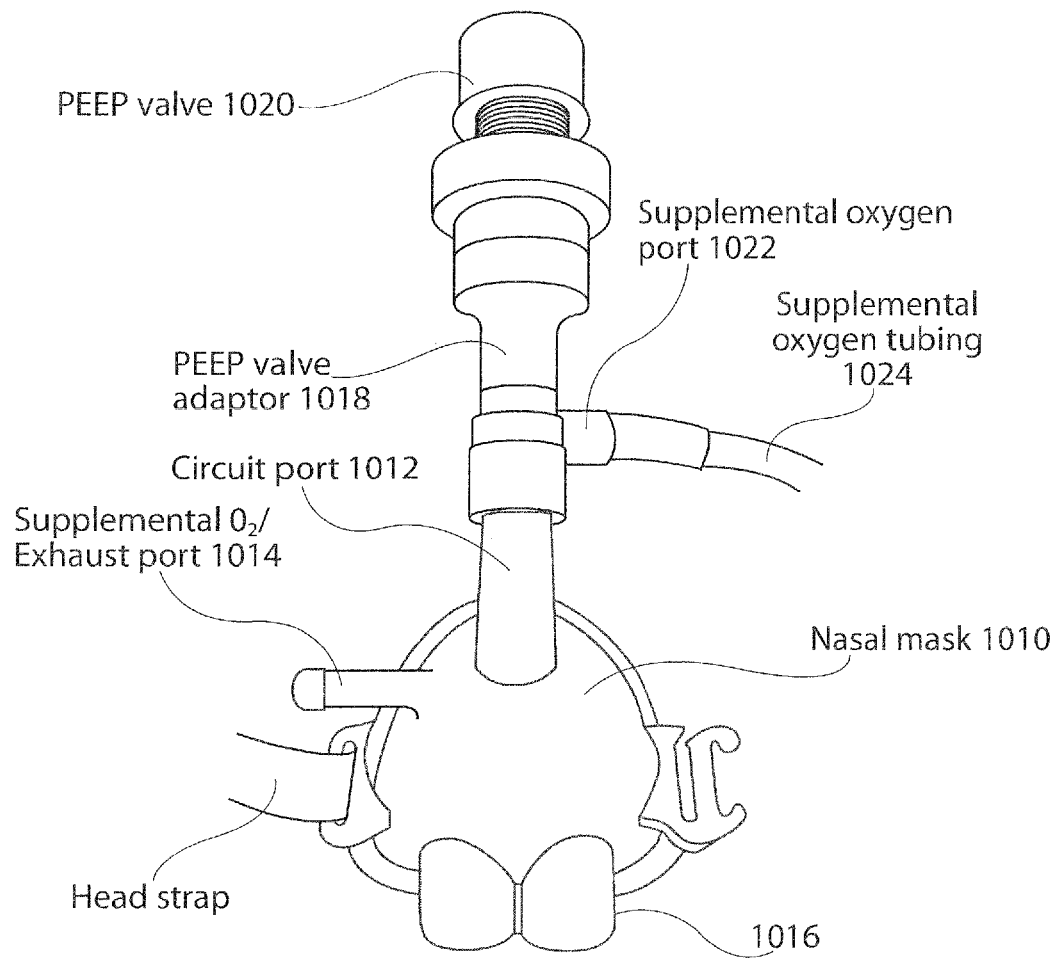
FIG. 25 is a perspective view of yet another embodiment of the invention showing a nasal mask with a peep valve adaptor.

Shown in FIG. 25 is a configuration for a combined disposable continuous positive airway pressure (CPAP) system and manual resuscitation system. The configuration consists of the following: a nasal chamber or nasal mask 1010 which has two ports, a circuit port 1012 and an exhaust port 1014 and one or more attachment ports 1016 which may include duck bill valves, a peep valve adaptor 1018, which connects to a positive end of an expiratory pressure (PEEP) valve 1020 and has a supplemental oxygen port 1022, which connects to supplemental oxygen source through tubing 1024. The circuit port 1012 attaches to adaptor 1018, which then attaches to the positive end expiratory pressure (PEEP) valve 1020 and applies a range of back-pressures to help stent open an obstructed airway and keep alveoli open, acting as a source for continuous positive airway pressure (CPAP). The exhaust port 1014 within the nasal mask 1020 is open to atmosphere and functions to prevent suffocation. Since the exhaust port 1014 is open to atmosphere a patient can inhale and exhale through it. It also prevents re-breathing of carbon dioxide ($CO_2$). This configuration can also be used as a manual resuscitation device intermittently covering the exhaust port, 1014, allowing pressure to be built up within the device and then uncovering the exhaust port and allowing for exhalation.

Figure 26:
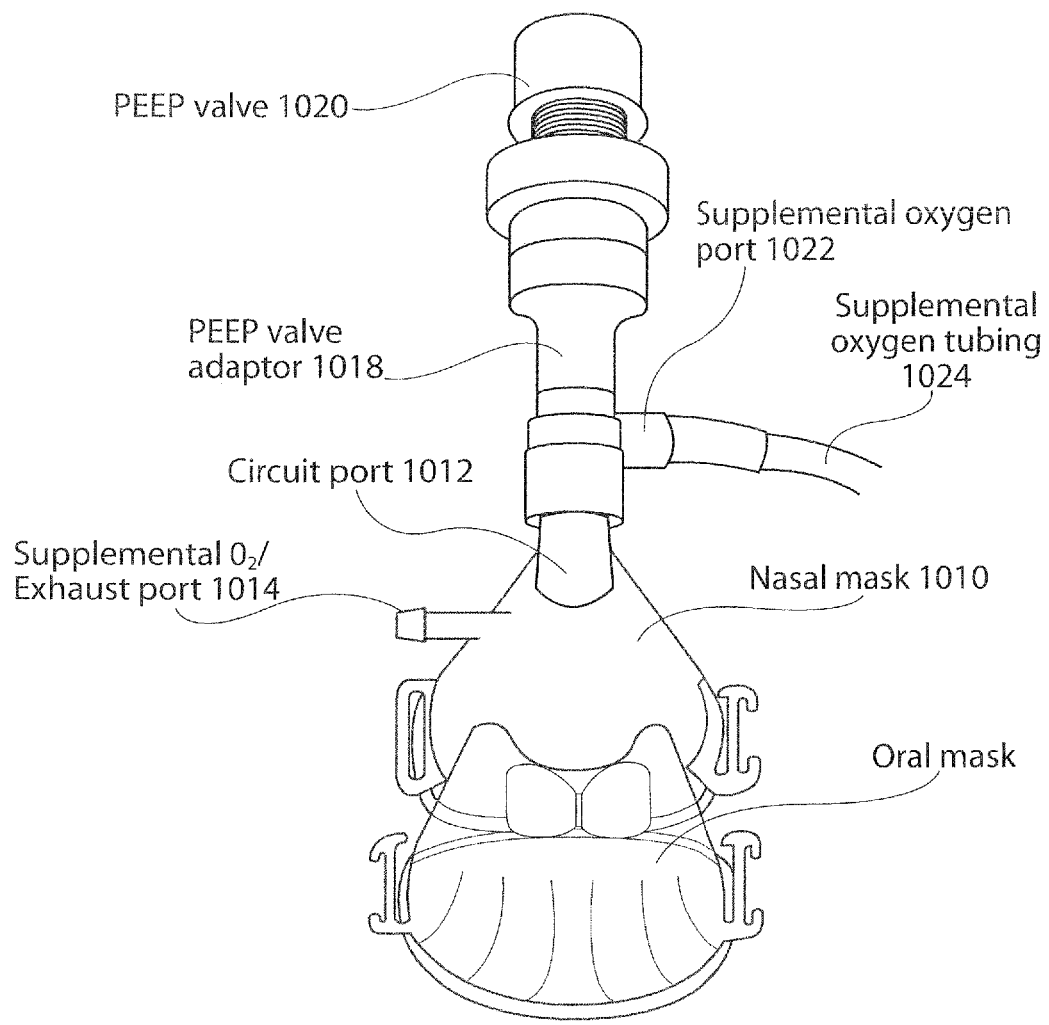
FIG. 26 is a view similar to FIG. 25, showing a two-piece (nasal and oral) mask incorporating a peep valve adaptor.

The duck bill valves within ports 116 of the nasal mask 1010 have three functions. Their first function is as an inhalation valve to allow the patient to inhale without much resistance. Their second function is to seal shut upon exhalation, which prevents excessive leaking and maintains positive pressure. Their third function is to permit attachment of different accessories. For example, as shown in FIG. 26, an oral chamber 1021 can be attached to the duck bill valves 1016. Within the oral chamber 1026 are proboscises (not shown) and when they are inserted into the duck bill valves 1016, the duck bill valves open i.e. as described in our aforesaid '934, '277 and '341 PCT Applications. This allows for bilateral flow through the nose and mouth, and converts the disposable nasal CPAP to a disposable full facemask CPAP.

The PEEP valve adaptor 1018 has two functions. The first function is that it has a supplemental oxygen port 1022 within it. The supplemental oxygen port is for connection to a supplemental oxygen source via supplemental oxygen tubing. This is what supplies oxygen (i.e.: gas flow) to the nasal mask and allows pressure to be built up within the mask. The second function of the adaptor is to connect to the PEEP valve 1020. The PEEP valve 1020 is the resistance that the patient has to exhale against. The PEEP valve 820 is adjustable from, e.g., 0 cm $H_2O$-30 cm $H_2O$.

Shown in FIG. 26 is a disposable CPAP system in accordance with the present invention is converted to a full facemask CPAP system. The oral chamber 1026 has two proboscises within it. When the oral chamber's proboscises are inserted into the nasal chamber's duck bill valves 1016, the duck bill valves 1016 open up and allow for bilateral flow through the nose and mouth of the patient, thus converting from a nasal CPAP mask to a full facemask CPAP. The advantage is that is allows for the pressure within the mask to be maintained without removing and replacing the mask with a full face mask Various changes may be made without departing from the spirit and the scope of the present invention. By way of example, while the nasal mask portion of the combination nasal/oral mask as described in our '973, '277 and '341 PCT applications and as commercially available as the SuperNO$_2$VA mask as described above, and including attachment ports duckbill valves is particularly useful for accepting accessories and attachments, other valves may be incorporated into the nasal mask. Also, it is not necessary that the attachment ports include valves which automatically close. In fact, simple removable plugs or frangible membranes could be employed in place of valves. Thus, any nasal mask having one or more sealable ports located over the upper lips of a patient may be advantageously adapted to support various attachments and accessories as above described. Also, in the case of end tidal CO$_2$ measurement, an exhalation scoop may be fixed directly or formed integrally with a lower portion conventional nasal mask, i.e., to lie adjacent the upper lip of a patient. Still other changes would be possible without departing from the spirit and scope of the invention.

What is claimed:

1. A breathing circuit adapted for delivering oxygen and/or anesthetic gases to a patient, the breathing circuit comprising:
    a fresh gas line;
    an exhalation collecting tube; and
    a two chamber ventilation facemask, the two chamber ventilation facemask comprising:
        a nasal chamber, the nasal chamber having a ventilation port, an end-tidal CO$_2$ port, a nasal bridge region, side walls and a lip region, wherein the nasal chamber is configured to extend over a nose of the patient and seal against the nasal bridge region and the lip region of the patient with the nose of the patient positioned within the nasal chamber, and
        an exhalation scoop integral with the nasal chamber and made of a flexible material;
    wherein the exhalation scoop is moveable between a first position, in which the exhalation scoop is configured to overly an upper lip of the patient, and a second position, in which the exhalation scoop is configured to allow access to a mouth of the patient to perform a procedure; and
    wherein the end-tidal CO$_2$ port is configured for scavenging gases, such that a gas adjacent to and overlying the upper lip of the patient can move to the end-tidal CO$_2$ port when the exhalation scoop is in the first position and the second position.

2. The breathing circuit of claim 1, wherein the exhalation collecting tube is configured to couple with the end-tidal CO$_2$ port and for connection to an end-tidal CO$_2$ monitor.

3. The breathing circuit of claim 2, wherein the exhalation collecting tube includes bacterial filters.

4. The breathing circuit of claim 1, wherein the nasal mask comprises a generally triangularly-shaped frame, and the nasal mask including a perimeter seal and a nasal bridge seal, the nasal bridge seal formed of an elastic membrane bridging the nasal bridge region and the perimeter seal.

5. The breathing circuit of claim 4, wherein the elastic membrane of the nasal bridge seal terminates at an inside edge of the perimeter seal.

6. The breathing circuit of claim 1, wherein the exhalation scoop forms an oral chamber.

7. The breathing circuit of claim 6, wherein the exhalation scoop is more flexible relative to the nasal chamber.

8. A method for delivering oxygen and/or anesthetic gases to a patient, comprising:
    providing a fresh gas line and an exhalation collecting line;
    connecting the fresh gas line and the exhalation collecting line to a two chamber ventilation facemask, the two chamber ventilation facemask comprising a nasal chamber and an exhalation scoop integral with the nasal chamber and made of a flexible material, the nasal chamber having a ventilation port, an end-tidal CO$_2$ port, a nasal bridge region, side walls, and a lip region such that the nasal chamber can extend over a nose of the patient and seal against the nasal bridge region and the lip region of the patient with the nose positioned within the nasal chamber; and
    moving the exhalation scoop between a first position, in which the exhalation scoop is configured to overlie an upper lip of the patient, and a second position, in which the exhalation scoop is configured to allow access to a mouth of the patient to perform a procedure, wherein the end-tidal CO$_2$ port is configured for scavenging gases, such that gas adjacent to the upper lip of the patient can move to the end-tidal CO$_2$ port when the exhalation scoop is in the first position and the second position.

9. The method of claim 8, wherein the exhalation collecting tube is configured to couple with the end-tidal CO$_2$ port and for connection to an end-tidal CO$_2$ monitor.

10. The method of claim 9, wherein the exhalation collecting tube includes bacterial filters.

11. The method of claim 8, wherein the exhalation scoop forms an oral chamber.

12. A breathing circuit adapted for delivering oxygen and/or anesthetic gases to a patient, the breathing circuit comprising:
    a fresh gas line;
    an exhalation collecting tube; and
    a two chamber ventilation facemask, the two chamber ventilation facemask comprising an exhalation scoop and a nasal chamber, the nasal chamber having a ventilation port, an end-tidal CO$_2$ port, a perimeter seal, and a nasal bridge seal, wherein the nasal chamber is configured to extend over a nose of the patient and seal against a nasal bridge region and a lip region of the patient with the nose of the patient positioned within the nasal chamber, wherein the exhalation scoop is integral with the nasal chamber and is made of a more flexible material, relative to the nasal chamber, wherein the exhalation scoop is movable between a first position, in which the exhalation scoop is configured to overlie an upper lip of the patient, and a second position, in which the exhalation scoop is configured to allow access to a mouth of the patient, and wherein the end-tidal CO$_2$ port is configured for scavenging gases, such that gas adjacent to the upper lip of the patient can move to the end-tidal CO$_2$ port when the exhalation scoop is in the first position and the second position.

* * * * *